US012678345B2

(12) United States Patent
Komatsubara et al.

(10) Patent No.: US 12,678,345 B2
(45) Date of Patent: Jul. 14, 2026

(54) ABSORBENT ARTICLE FOR PET

(71) Applicant: Unicharm Corporation, Ehime-ken (JP)

(72) Inventors: Daisuke Komatsubara, Kanonji (JP); Yumi Matsumoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 452 days.

(21) Appl. No.: 18/173,932

(22) Filed: Feb. 24, 2023

(65) Prior Publication Data

US 2023/0190543 A1 Jun. 22, 2023

Related U.S. Application Data

(63) Continuation of application No. PCT/JP2020/041760, filed on Nov. 9, 2020.

(30) Foreign Application Priority Data

Aug. 31, 2020 (JP) ................................. 2020-146275

(51) Int. Cl.
*A61F 13/511* (2006.01)
*A01K 23/00* (2006.01)
*A61F 13/15* (2006.01)

(52) U.S. Cl.
CPC .......... *A61F 13/5116* (2013.01); *A01K 23/00* (2013.01); *A61F 2013/15186* (2013.01)

(58) Field of Classification Search
CPC ......... A61F 2013/15186; A61F 13/494; A01K 23/00
See application file for complete search history.

(56) References Cited

U.S. PATENT DOCUMENTS 5,558,659 A 9/1996 Sherrod et al.
8,992,495 B1 3/2015 Howell
(Continued)

FOREIGN PATENT DOCUMENTS

CN 103476247 A 12/2013
CN 103561565 A 2/2014
(Continued)

OTHER PUBLICATIONS

English translation of JP 2007020533 A.*
(Continued)

*Primary Examiner* — Jessica Arble
(74) *Attorney, Agent, or Firm* — Osha Bergman Watanabe & Burton LLP

(57) ABSTRACT

An absorbent article for a pet includes: a liquid absorber disposed between a liquid-permeable top sheet and a liquid-impermeable back surface layer; a first leakage suppressing portion including a first joining portion that is joined to the liquid-permeable top sheet and a first rising portion that is not joined to the liquid-permeable top sheet; and a second leakage suppressing portion including a second joining portion that is joined to the liquid-permeable top sheet and a second rising portion that is not joined to the liquid-permeable top sheet. The first and second leakage suppressing portions are disposed on a side of the liquid-permeable top sheet along a longitudinal direction on two widthwise sides of the absorbent article. A longitudinal contracting force in the second rising portion is smaller than a longitudinal contracting force in the first rising portion.

28 Claims, 12 Drawing Sheets

(56) References Cited

U.S. PATENT DOCUMENTS

| | | | |
|---|---|---|---|
| 2003/0158530 A1 | 8/2003 | Diehl et al. | |
| 2005/0154367 A1 | 7/2005 | Ikegami | |
| 2006/0224132 A1 | 10/2006 | Roe et al. | |
| 2006/0282055 A1* | 12/2006 | Shiomi | A61F 13/471 |
| | | | 604/385.19 |
| 2009/0326494 A1 | 12/2009 | Uchida et al. | |
| 2011/0209675 A1 | 9/2011 | Esperon | |
| 2014/0090608 A1 | 4/2014 | Komatsubara et al. | |
| 2014/0109843 A1* | 4/2014 | Komatsubara | A01K 23/00 |
| | | | 119/869 |
| 2014/0165926 A1 | 6/2014 | Marks | |
| 2015/0173968 A1 | 6/2015 | Joseph | |
| 2015/0196009 A1* | 7/2015 | Komatsubara | B31D 1/04 |
| | | | 493/356 |
| 2019/0008706 A1* | 1/2019 | Saito | A61F 13/496 |
| 2019/0060130 A1* | 2/2019 | Tally | A61F 13/64 |
| 2020/0000061 A1 | 1/2020 | Yamamoto et al. | |
| 2023/0190543 A1 | 6/2023 | Komatsubara et al. | |

FOREIGN PATENT DOCUMENTS

| | | | | |
|---|---|---|---|---|
| CN | 104853601 A | | 8/2015 | |
| CN | 104869815 A | | 8/2015 | |
| CN | 106132195 A | | 11/2016 | |
| CN | 207443944 U | | 6/2018 | |
| CN | 109310067 A | | 2/2019 | |
| JP | 2004-159592 A | | 6/2004 | |
| JP | 2007020533 A | * | 2/2007 | |
| JP | 2008-104850 A | | 5/2008 | |
| JP | 2008-104889 A | | 5/2008 | |
| JP | 3143754 U | | 8/2008 | |
| JP | 2009-254278 A | | 11/2009 | |
| JP | 2012-178976 A | | 9/2012 | |
| JP | 2012-205579 A | | 10/2012 | |
| JP | 2012187095 A | | 10/2012 | |
| JP | 2013-000034 A | | 1/2013 | |
| JP | 2013046587 A | | 3/2013 | |
| JP | 5902863 B1 | | 3/2016 | |
| JP | 2016112217 A | | 6/2016 | |
| JP | 6308121 B2 | | 4/2018 | |
| JP | 2019-110862 A | | 7/2019 | |
| JP | 2020-000172 A | | 1/2020 | |
| TW | 201717748 A | | 6/2017 | |
| WO | WO-2019131066 A1 | * | 7/2019 | A01K 23/00 |

OTHER PUBLICATIONS

Office Action issued in corresponding Chinese Application No. 202080103411.7 mailed Jul. 7, 2024 (With Partial Translation).

International Search Report issued in International Application No. PCT/JP2020/041760 mailed Dec. 28, 2020 (6 pages).

International Search Report issued in related International Application No. PCT/JP2020/041708, dated Dec. 28, 2020, with translation (6 pages).

Office Action issued in related U.S. Appl. No. 18/173,409 mailed Aug. 15, 2024 (26 pages).

Office Action issued in corresponding Chinese Patent Application No. 202080103422.5, dated Jun. 6, 2025, with partial translation (11 pages).

Office Action issued in related U.S. Appl. No. 18/173,409, mailed May 28, 2025 (16 pages).

Search Report issued in corresponding Chinese Application No. 202080103422.5 mailed Apr. 30, 2026 (6 pages).

* cited by examiner

ABSORBENT ARTICLE FOR PET

BACKGROUND

Technical Field

The present invention relates to an absorbent article for a pet.

Description of the Related Art

Conventionally, as an article for collecting urine excreted by a pet, particularly a dog or a cat, a belt-like absorbent article that is put on in a state where the absorbent article is wrapped around the waist of the pet without covering the entire bottom portion is known (for example, Patent Literature 1). In the absorbent article described in Patent Literature 1, excreted urine is collected in the absorber included in the absorbent component by putting on the absorbent article so as to cover the urethral opening of a pet. Therefore, for example, even when the marking is done based on the behavior of a dog, dirt with urine can be suppressed.

PATENT LITERATURE

Patent Literature 1: Japanese Patent Application Publication No. 2007-020533

In the absorbent article described in Patent Literature 1, in order to suppress urine leakage, belt-like three-dimensional gathers are provided on both the foreleg side and the hind leg side of the surface that comes into contact with the waist of the pet. Of these three-dimensional gathers, the three-dimensional gather on the hind leg side is arranged at a position that exactly overlaps the sex organ of a male pet while the absorbent article is put on. Therefore, when the male pet in the absorbent article moves, there is a risk that the three-dimensional gather and the sex organ are rubbed to cause skin inflammation such as rash or redness.

SUMMARY

One or more embodiments may provide an absorbent article for a pet capable of suppressing rubbing against a sex organ while the absorbent article is put on.

One or more embodiments may include the following aspects.

[1] An absorbent article for a pet that has a longitudinal direction, a width direction, and a thickness direction which are orthogonal to each other and is put on such that the longitudinal direction extends along a waist direction of the pet, the absorbent article comprising: a top sheet that is permeable to a liquid; a back surface layer that is impermeable to the liquid; an absorber that is arranged between the top sheet and the back surface layer and absorbs the liquid; and a pair of a first leakage suppressing portion and a second leakage suppressing portion that are provided on a top sheet side, wherein the first leakage suppressing portion and the second leakage suppressing portion are provided along the longitudinal direction on two widthwise sides, the first leakage suppressing portion has a first joining portion that is joined to the top sheet, and a first rising portion that is not joined to the top sheet, the second leakage suppressing portion has a second joining portion that is joined to the top sheet, and a second rising portion that is not joined to the top sheet, and a longitudinal contracting force in the second rising portion is smaller than a longitudinal contracting force in the first rising portion.

[2] The absorbent article for a pet according to [1], wherein the first leakage suppressing portion has a first suppressing portion main body that is formed using a hydrophobic nonwoven fabric as a material, and a first elastic member that is attached in a longitudinal direction of the first suppressing portion main body in the first rising portion, the second leakage suppressing portion has a second suppressing portion main body that is formed using a hydrophobic nonwoven fabric as a material, and a second elastic member that is attached in a longitudinal direction of the second suppressing portion main body in the second rising portion, and the number of the second elastic members is smaller than the number of the first elastic members.

[3] The absorbent article for a pet according to [1], wherein the first leakage suppressing portion has a first suppressing portion main body that is formed using a hydrophobic nonwoven fabric as a material, and an elastic member that is attached in a longitudinal direction of the first suppressing portion main body in the first rising portion, and the second leakage suppressing portion has a second suppressing portion main body that is formed using a hydrophobic nonwoven fabric as a material, and does not have an elastic member that makes the second suppressing portion main body contract in the longitudinal direction.

[4] The absorbent article for a pet according to [2] or [3], wherein a pair of short sides of the second suppressing portion main body are weakly joined to the top sheet, one of a pair of long sides of the second suppressing portion main body positioned on an outer peripheral side of the top sheet is joined to the top sheet and the back surface layer, and the other of the pair of long sides positioned on an inner peripheral side of the top sheet is not joined to the top sheet.

[5] The absorbent article for a pet according to any one of [1] to [4], wherein the second rising portion has a narrow portion having a narrower width at a longitudinal central part of the second rising portion.

[6] The absorbent article for a pet according to any one of [1] to [5], wherein a flap portion that extends in a longitudinal direction of the top sheet and the back surface layer is provided on a widthwise outermost side of the top sheet and the back surface layer, the top sheet and the back surface layer are folded back so that the flap portion faces the top sheet in a posture in which the top sheet and the back surface layer warp the second rising portion inside to form a fold line in the longitudinal direction of the top sheet and the back surface layer, and the fold line overlaps the second rising portion.

[7] The absorbent article for a pet according to any one of [1] to [5], wherein a flap portion that extends in a longitudinal direction of the top sheet and the back surface layer is provided on a widthwise outermost side of the top sheet and the back surface layer, the top sheet and the back surface layer are folded back so that the flap portion faces the top sheet in a posture in which the top sheet and the back surface layer warp the second rising portion inside to form a fold line in the longitudinal direction of the top sheet and the back surface layer, and the fold line is positioned on an inner peripheral side of the top sheet with respect to the second rising portion.

[8] The absorbent article for a pet according to any one of [1] to [7], wherein a sum of a distance from a widthwise head side end of the absorber to the first joining portion and a distance from the first joining portion to an end of the first rising portion is longer than a sum of a distance from a widthwise bottom side end of the absorber to the second joining portion and a distance from the second joining portion to an end of the second rising portion, at a longitudinal central part.

[9] The absorbent article for a pet according to [8], wherein the distance from the first joining portion to the end of the first rising portion is longer than the distance from the second joining portion to the end of the second rising portion at the central part.

[10] The absorbent article for a pet according to [8] or [9], wherein the distance from the widthwise head side end of the absorber to the first joining portion is longer than the distance from the widthwise bottom side end of the absorber to the second joining portion at the central part.

[11] The absorbent article for a pet according to any one of [1] to [10], wherein the first leakage suppressing portion has, at two longitudinal end portions, third joining portions that are joining portions between the first leakage suppressing portion and the top sheet, and a distance from the third joining portion to an end of the first rising portion is shorter than a distance from the second joining portion to an end of the second rising portion in the width direction.

[12] The absorbent article for a pet according to any one of [1] to [11], wherein the absorber protrudes toward a direction of the second leakage suppressing portion at a longitudinal central part of the top sheet.

[13] The absorbent article for a pet according to any one of [1] to [12], wherein the back surface layer has a color change portion that reacts with the liquid and changes a color, and the color change portion is positioned on a second joining portion side with respect to a central position between the first joining portion and the second joining portion.

[14] The absorbent article for a pet according to any one of [1] to [13], further comprising: a locking portion that connects the top sheet and the back surface layer at two longitudinal end portions.

[15] The absorbent article for a pet according to [14], wherein the locking portion is provided on the back surface layer.

[16] The absorbent article for a pet according to [14] or [15], wherein the back surface layer has a mark portion that indicates a position of a longitudinal end of the back surface layer arranged on an outer side in a state of being fixed in a cylindrical shape by the locking portion, the mark portion has a first mark portion that is positioned on a widthwise head side of the back surface layer, and a second mark portion that is positioned on a widthwise bottom side of the back surface layer, and the second mark portion is positioned on a longitudinal inner side with respect to the first mark portion.

[17] The absorbent article for a pet according to any one of [14] to [16], wherein a widthwise center of the locking portion is positioned on a second joining portion side with respect to a central position between the first joining portion and the second joining portion.

[18] The absorbent article for a pet according to any one of [14] to [17], wherein a region in which the locking portion is provided has a high stiffness region having a relatively high stiffness in the region.

[19] The absorbent article for a pet according to [18], wherein the locking portion is provided in the width direction of the back surface layer, and the high stiffness region is positioned on a widthwise head side.

According to one or more embodiments, an absorbent article for pets capable of suppressing rubbing against a sex organ while the absorbent article is put on can be provided.

4

DESCRIPTION OF THE EMBODIMENTS

First Example

Hereinafter, an absorbent article for a pet according to a first example will be described with reference to FIGS. 1 to 14. It should be noted that, in all of the following drawings, in order to make the drawings easier to see, dimensions, ratios, or the like of the respective constituent elements is appropriately changed. Further, in the following description, the absorbent article for a pet will sometimes be simply referred to as an "absorbent article".

Figure 1:
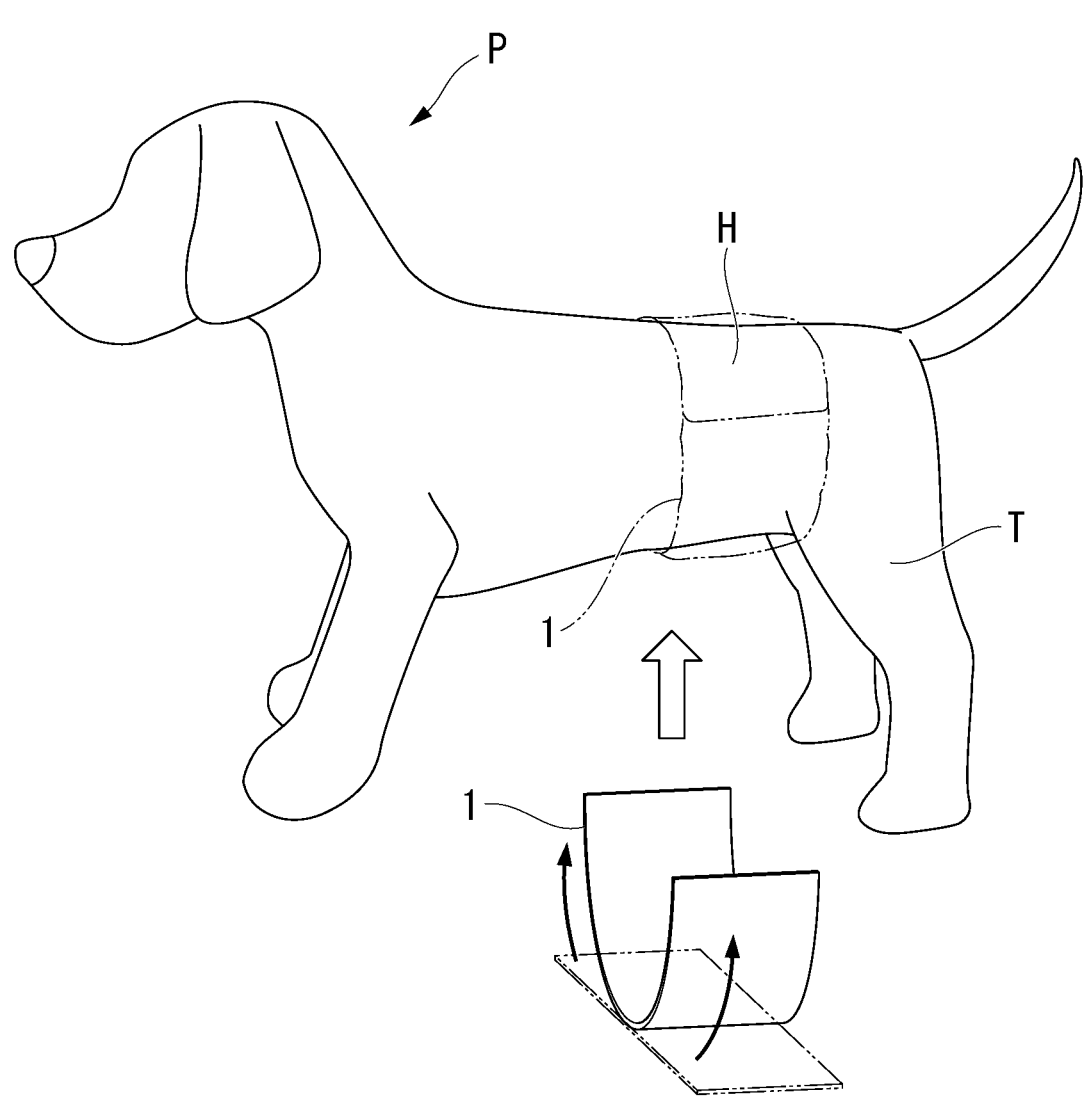
FIG. 1 is a schematic view showing a putting state of an absorbent article for a pet according to one or more embodiments.

FIG. 1 is a schematic view showing a putting state of the absorbent article for a pet 1 according to one or more embodiments. The absorbent article 1 is suitably used for male pets. The absorbent article 1 absorbs and keeps the liquid discharged from a pet P therein. The liquid to be absorbed refers to a liquid substance discharged from the body of the pet P, and typically includes urine discharged by the pet P. Other examples thereof include blood and semen. Hereinafter, the absorbent article 1 will be described using urine as an example of the liquid to be absorbed.

In the following description, an example is given in which a pet to put on the absorbent article 1 is a dog, but the absorbent article 1 may be put on another pet. For example, the absorbent article 1 may be put on a cat.

The absorbent article 1 of one or more embodiments has a belt-like shape and has a longitudinal direction, a width direction, and a thickness direction that are orthogonal to each other. As shown in FIG. 1, the absorbent article 1 is put on such that the longitudinal direction extends along the waist direction of the pet P, and is wrapped around a waist H of the pet P in the front side (head side) of a thigh portion T of the pet P.

In one or more embodiments, the term "belt-like" is an expression showing a state of long extension in one direction. In this sense, the term "belt-like shape" is not limited to a mathematical rectangular shape, and the shape of a side may not be necessarily a linear line.

When the absorbent article 1 is put on the pet in such a posture, the absorbent article 1 covers the urethral opening of the pet P, which makes it possible to absorb and keep urine excreted by the pet P therein.

In the following description, in the absorbent article 1, a surface that faces the pet P while the absorbent article 1 is put on will be referred to as a "front surface", and a surface that faces toward the outer side, which is opposite to the pet P, while the absorbent article 1 is put on will be referred to as a "back surface".

Figure 2:
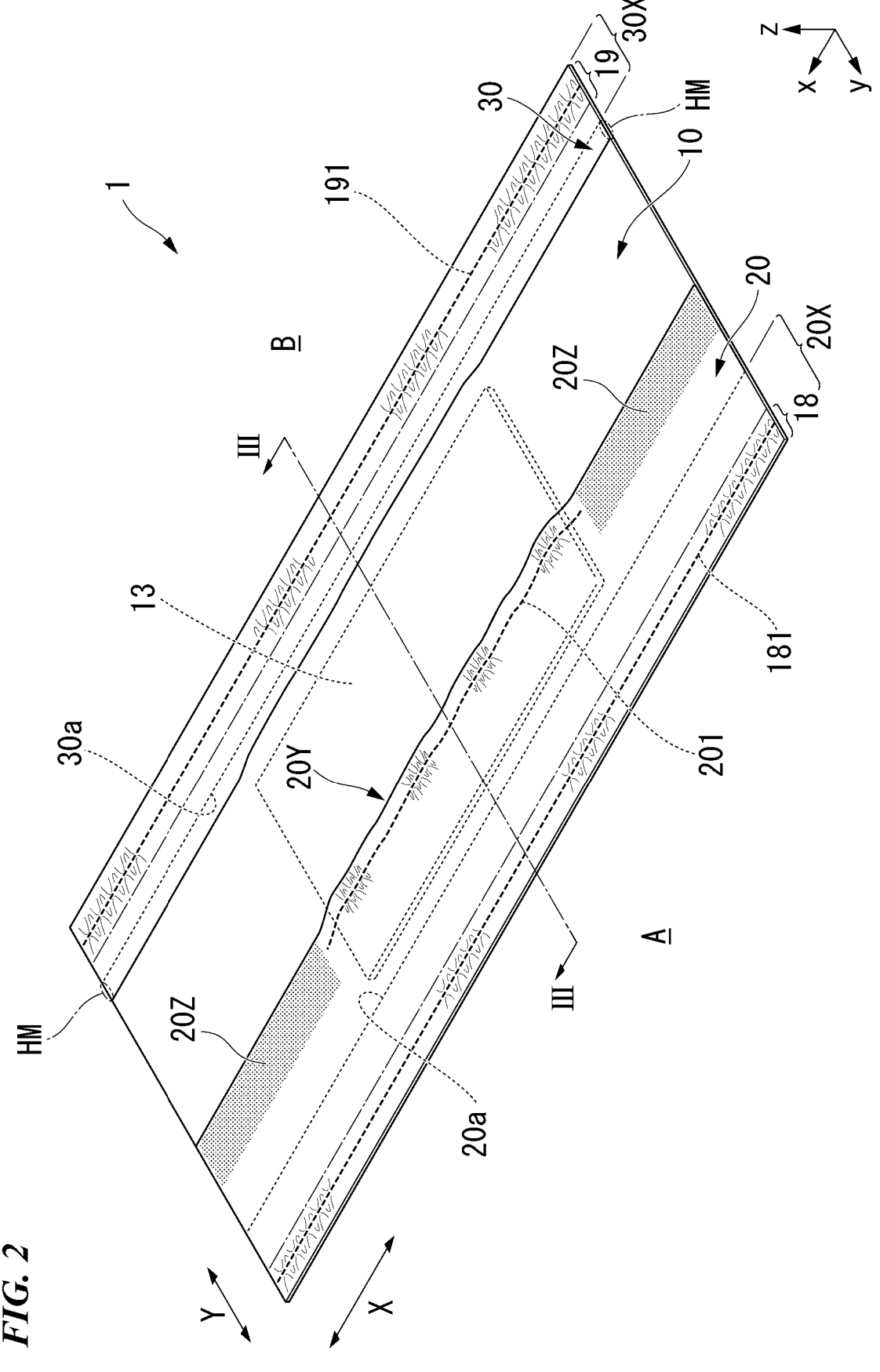
FIG. 2 is a schematic perspective view showing the absorbent article for a pet according to one or more embodiments.
Figure 3:
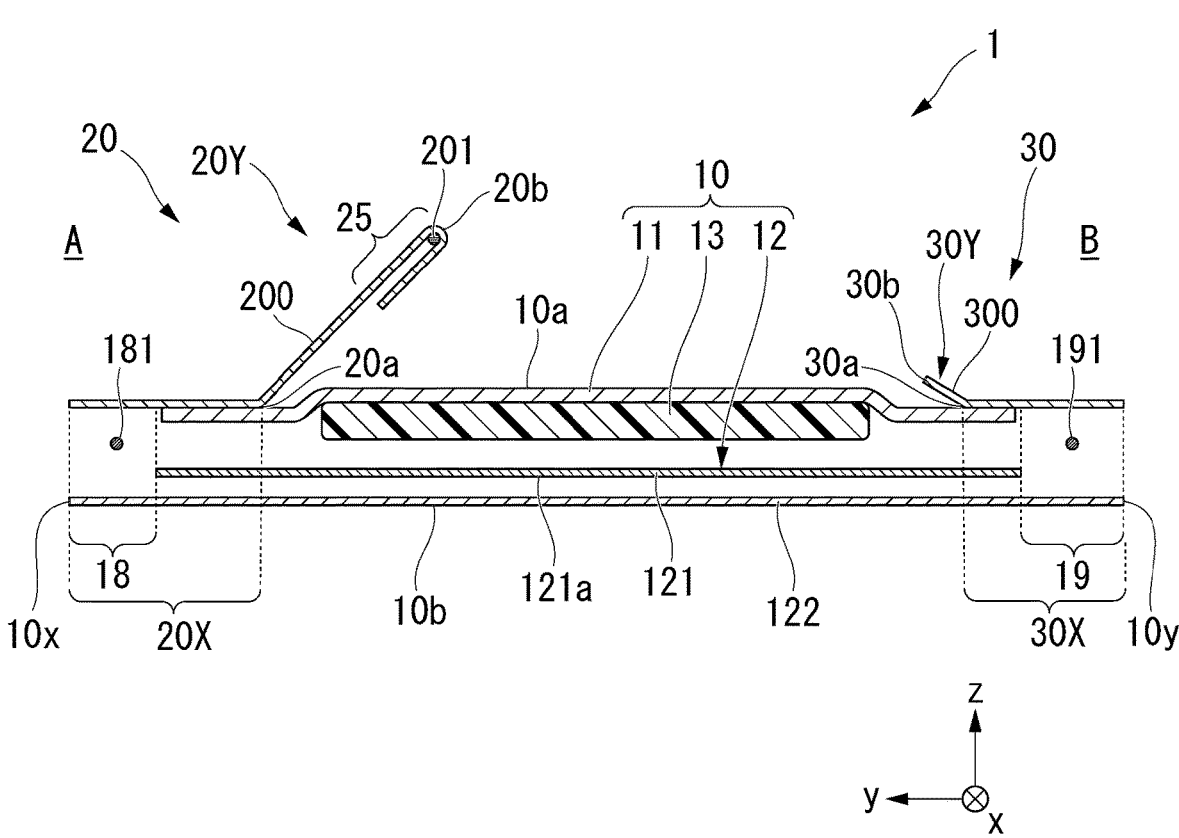
FIG. 3 is an exploded cross-sectional view in a cross-sectional field of view shown by a line segment in FIG. 2.
Figure 4:
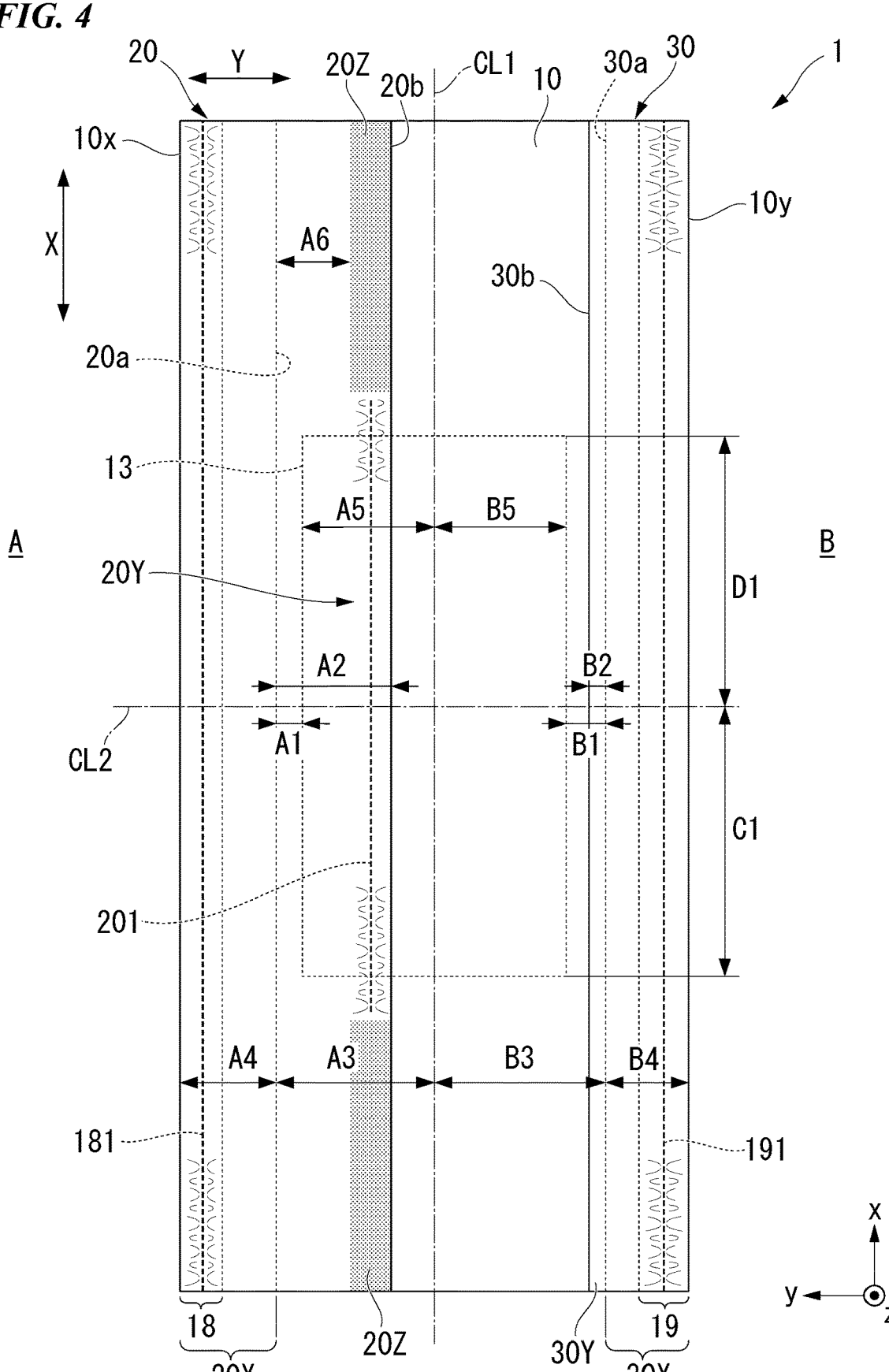
FIG. 4 is a plan view of the absorbent article for a pet.

FIG. 2 is a schematic perspective view showing the absorbent article 1 according to one or more embodiments. FIG. 3 is an exploded cross-sectional view in a cross-sectional field of view shown by a line segment in FIG. 2. FIG. 4 is a plan view of the absorbent article 1.

In the following description, an xyz orthogonal coordinate system is set, and the positional relationship between the constituent members will be described with reference to the xyz orthogonal coordinate system. Here, a predetermined direction in the horizontal plane is defined as an x-axis direction, a direction that is orthogonal to the x-axis direction in the horizontal plane is defined as a y-axis direction, and a direction that is orthogonal to the x-axis direction and the y-axis direction (that is, a vertical direction) is defined as a z-axis direction.

As shown in FIGS. 2 and 3, the absorbent article 1 of one or more embodiments includes a main body portion 10, and a pair of first leakage suppressing portion 20 and a second leakage suppressing portion 30.

In the absorbent article 1, in the putting state shown in FIG. 1, the head side of the pet P is denoted by reference sign A, and in the putting state, the bottom side of the pet P is denoted by reference sign B.

(Main Body Portion)

The main body portion 10 has a belt-like appearance that extends in the x-axis direction. The length of the main body portion 10 in the y-axis direction is shorter than the length of the main body portion 10 in the x-axis direction. The x-axis direction corresponds to the "longitudinal direction" in one or more embodiments. Further, the y-axis direction corresponds to the "width direction" in the one or more embodiments. Further, the z-axis direction corresponds to the "thickness direction" in one or more embodiments.

The longitudinal direction of the main body portion 10 is denoted by reference sign X, and the width direction of the main body portion 10 is denoted by reference sign Y.

The main body portion 10 has a top sheet (or a liquid-permeable top sheet) 11, a back surface layer (or a liquid-impermeable back surface layer) 12, and an absorber (or a liquid absorber) 13. The top sheet 11, the back surface layer 12, and the absorber 13 are overlaid in the thickness direction (z-axis direction).

The top sheet 11 is positioned on a front surface 10*a* side of the main body portion 10 and constitutes the front surface 10*a* of the main body portion 10.

The top sheet 11 is permeable to a liquid (urine of the pet P). The top sheet 11 is formed of, for example, a nonwoven fabric.

The back surface layer 12 is positioned on a back surface 10*b* side of the main body portion 10 and constitutes the back surface 10*b* of the main body portion 10. The back surface layer 12 is impermeable to a liquid (urine of the pet P).

The back surface layer 12 has a waterproof film 121 that is impermeable to the urine of the pet P, and a nonwoven fabric 122 provided on the outer side with respect to the waterproof film 121.

Printing may be performed on a surface 121*a* on the back surface side of the waterproof film 121. Further, printing may be performed on the nonwoven fabric 122.

In the absorbent article 1 shown in FIG. 3, the widthwise length of the top sheet 11 matches the widthwise length of the waterproof film 121. Further, the widthwise length of the nonwoven fabric 122 is longer than the widthwise length of the top sheet 11 and the widthwise length of the waterproof film 121. The nonwoven fabric 122 completely covers the top sheet 11 and the waterproof film 121 in the field of view from the back surface.

The absorber 13 is arranged between the top sheet 11 and the back surface layer 12. The absorber 13 absorbs a liquid (urine of the pet P). As shown in FIG. 2, the absorber 13 extends in the longitudinal direction X of the absorbent article 1 and is arranged at the center of the absorbent article in the longitudinal direction X. The length of the absorber 13 in the width direction Y is shorter than the length of the absorber 13 in the longitudinal direction X.

The absorber 13 can employ a well-known configuration as an absorber of an absorbent article for a pet. For example, the absorber 13 is a member having a core formed of an absorbent material as a material and a wrap material that wraps the core, and has a rectangular shape in a plan view.

As the absorbent material, fluff pulp and superabsorbent polymer can be exemplified. As the fluff pulp, chemical pulp, cellulose fibers, artificial cellulose fibers such as rayon, acetate, and the like can be exemplified. As the superabsorbent polymer, starch-based, acrylic acid-based, and amino acid-based granulous or fibrous polymers can be exemplified.

As the wrap material, a nonwoven fabric wrap and a tissue wrap can be exemplified.

(First Leakage Suppressing Portion)

The first leakage suppressing portion 20 is provided on the top sheet 11 side of the main body portion 10. The first leakage suppressing portion 20 is a belt-like member that extends along the longitudinal direction X of the main body portion 10.

The first leakage suppressing portion 20 has a first suppressing portion main body 200 that is formed using a hydrophobic nonwoven fabric as a material and extends in the longitudinal direction X, and an elastic member 201 that is attached along the longitudinal direction of the first suppressing portion main body 200. The nonwoven fabric that is the material of the first leakage suppressing portion 20 may be subjected to a water repellent treatment.

It should be noted that in the following description, the term "end portion" refers to a region that includes a certain range including the end edge of the article.

Further, the term "end" refers to the end edge of the article. The same applies to the terms "one end" and "other end".

The first leakage suppressing portion 20 has a first joining portion 20X that is a region joined to the main body portion 10 and a first rising portion 20Y that is a region not joined to the main body portion 10.

The first joining portion 20X is the end portion on the head side A of the first leakage suppressing portion 20 in the width direction Y and is a region that is joined to the main body portion 10 (the top sheet 11 and the back surface layer 12). The first joining portion 20X is provided along the longitudinal direction X at the end portion on the head side A of the first leakage suppressing portion 20. As the joining method, fusion or gluing may be used.

The first rising portion 20Y is the end portion on the bottom side B of the first leakage suppressing portion 20 in the width direction Y and is a region that is not joined to the main body portion 10. The first rising portion 20Y is provided along the longitudinal direction X at the end portion on the bottom side B of the first leakage suppressing portion 20.

Further, as shown in FIG. 4, the first leakage suppressing portion 20 may be provided with third joining portions 20Z that are joined to the top sheet 11. In one or more embodiments, the third joining portion 20Z is the end portion on the bottom side B of the first leakage suppressing portion 20 in the width direction Y and are provided at two end portions in the longitudinal direction X.

In a case where the first leakage suppressing portion 20 is joined to the top sheet 11 in the third joining portion 20Z, the range of the first rising portion 20Y refers to the end portion on the bottom side B of the first leakage suppressing portion 20 in the width direction Y and a region in which the third joining portion 20Z is not provided.

In the first rising portion 20Y, the inner end portion of the first suppressing portion main body 200 in the width direction Y is folded back along the longitudinal direction X while wrapping the elastic member 201. As shown in FIG. 2, the elastic member 201 is provided in the vicinity of the center of the main body portion 10 in the longitudinal direction X, and a part of the elastic member 201 is fixed in a state of being stretched in the longitudinal direction X at the time of manufacturing. The elastic member 201 is released from the force applied to stretch the elastic member 201 at the time of manufacturing, and contracts in the longitudinal direction X based on the contracting force (elastic force) of the elastic member 201.

As the material of the elastic member 201, any material that is elongated and stretchable may be used. As the material of the elastic member 201, specifically, natural rubber such as filiform rubber and flat rubber, and thermoplastic elastomer such as urethane, ethylene-vinyl acetate copolymer (EVA), and PE. As the thermoplastic elastomer, polybutadiene, polyisoprene, styrene-butadiene copolymer, styrene-isoprene copolymer, polyurethane, ethylene-vinyl acetate copolymer, ethylene-α-olefin copolymer and the like that are molded into a filiform shape or formed into a film and then slit into thin strips can be exemplified.

The belt-like region that is the inner end portion of the first suppressing portion main body 200 and is folded-back is joined to the facing first suppressing portion main body 200. In the first rising portion 20Y, a portion to which the first suppressing portion main body 200 is joined while wrapping the elastic member 201 constitutes the gather portion 25. The gather portion 25 has a configuration known as a three-dimensional gather.

The region in which the gather portion 25 is formed contracts in conjunction with the contraction of the elastic member 201. Therefore, the first rising portion 20Y contracts in the longitudinal direction X of the first rising portion 20Y.

Further, the first leakage suppressing portion 20 is joined to the nonwoven fabric 122 of the main body portion 10 at the end portion on the head side A of the first leakage suppressing portion 20 in the width direction Y in a state where an elastic member 181 is interposed between the first leakage suppressing portion 20 and the nonwoven fabric 122. The elastic member 181 is provided along the longitudinal direction X of the main body portion 10 and is fixed in a state of being stretched in the longitudinal direction X. In the first leakage suppressing portion 20, a portion that has the elastic member 181 interposed with the nonwoven fabric 122 and is joined to the nonwoven fabric 122 of the main body portion 10 constitutes a first flap portion 18. The first flap portion 18 is positioned on the outermost side on the head side A of the main body portion 10 in the width direction Y and extends in the longitudinal direction X.

As the material of the elastic member 181, the material similar to the material of the elastic member 201 can be used.

(Second Leakage Suppressing Portion)

The second leakage suppressing portion 30 is provided on the top sheet 11 side of the main body portion 10. The second leakage suppressing portion 30 is a belt-like member that extends along the longitudinal direction X of the main body portion 10. Further, the width of the second leakage suppressing portion 30 is narrower than the width of the first leakage suppressing portion 20.

The second leakage suppressing portion 30 has a second suppressing portion main body 300 that is formed using a hydrophobic nonwoven fabric as a material and extends in the longitudinal direction X. The nonwoven fabric which is the material of the second leakage suppressing portion 30 may be subjected to a water repellent treatment.

The second leakage suppressing portion 30 has a second joining portion 30X that is a region joined to the main body portion 10, and a second rising portion 30Y that is a region not joined to the main body portion 10.

The second joining portion 30X is the end portion on the bottom side B of the second leakage suppressing portion 30 in the width direction Y and is a region that is joined to the main body portion 10 (the top sheet 11 and the back surface layer 12). The second joining portion 30X is provided along the longitudinal direction X at the end portion on the bottom side B of the second leakage suppressing portion 30. As the joining method, fusion or gluing may be used.

The second rising portion 30Y is the end portion on the head side A of the second leakage suppressing portion 30 in the width direction Y and is a region that is not joined to the main body portion 10. The second rising portion 30Y is provided along the longitudinal direction X at the end portion on the head side A of the second leakage suppressing portion 30.

The second rising portion 30Y does not have an elastic member that contracts the second rising portion 30Y in the longitudinal direction unlike the first rising portion 20Y.

Two end portions of the second rising portion 30Y in the longitudinal direction X may be weakly joined to the top sheet 11. In FIG. 2, the weakly joined portion is denoted by reference sign HM.

Weak joining refers to joining with strength to the extent that while in a case where a force applied to the joining portion is weak (for example, in a case where a force to the extent that the folded absorbent article for a pet 1 is unfolded is indirectly transmitted to the joining portion), the joining state is maintained, in a case where a predetermined force or more is applied to the joining portion (for example, in a case where a force is applied to the joining portion in a direction of releasing the joining due to the movement of a pet as a putting target in a state where the joining portion is in contact with the pet), the joining state is released.

Further, the second leakage suppressing portion 30 is joined to the nonwoven fabric 122 of the main body portion 10 at the end portion on the bottom side B of the second leakage suppressing portion 30 in the width direction Y in a state where an elastic member 191 is interposed between the second leakage suppressing portion 30 and the nonwoven fabric 122. The elastic member 191 is provided along the longitudinal direction X of the main body portion 10 and is fixed in a state of being stretched in the longitudinal direction X. In the second leakage suppressing portion 30, a portion that has the elastic member 191 interposed with the nonwoven fabric and is joined to the nonwoven fabric 122 of the main body portion 10 constitutes a second flap portion 19. The second flap portion 19 is positioned on the outermost side of the main body portion 10 (the top sheet 11 and the back surface layer 12) in the width direction Y and extends in the longitudinal direction X.

As the material of the elastic member 191, the material similar to the material of the elastic member 201 mentioned above can be used.

As described above, while the first rising portion 20Y has the elastic member 201 and contracts in the longitudinal direction, the second rising portion 30Y does not have the elastic member and does not contract in the longitudinal direction. That is, the contracting force in the longitudinal direction X in the second rising portion 30Y is smaller than the contracting force in the longitudinal direction X in the first rising portion 20Y.

The contracting force of the first rising portion 20Y and the second rising portion 30Y is obtained by cutting a strip-like test piece along the longitudinal direction X from the first rising portion 20Y and the second rising portion 30Y, and measuring the tensile load.

The test piece is prepared as follows.

First, the absorbent article 1 is unfolded and stretched in the longitudinal direction X to an extent that wrinkles (gathers) formed by the contraction action of the elastic member 181 are no longer present on the surface of the first rising portion 20Y. Next, the strip-like test piece is cut from the first rising portion 20Y and the second rising portion 30Y of the absorbent article 1 in a stretched state.

When the test piece is cut out from the first rising portion 20Y, the test piece is prepared so that the gather portion 25 is included in the entire region in the longitudinal direction of the test piece.

That is, in a case where the test piece includes a region in which the gather portion 25 is not present in the longitudinal direction X of the first rising portion 20Y, the test piece is cut out so as not to include the "region in which the gather portion 25 is not present".

The dimension of the test piece in a state when the test piece is cut off, that is, in a state where the absorbent article 1 is stretched to an extent that there is no wrinkle (gather) in the longitudinal direction X, are defined as an initial dimension of the test piece.

The tensile load (N) of each of the prepared test pieces is measured using an autograph type tensile testing machine (Model No. AG-1KN1, manufactured by Shimadzu Corporation).

In a state where one longitudinal end portion of each test piece is sandwiched between fixed chucks, and the other longitudinal end portion of each test piece is sandwiched between movable chucks, the movable chucks are moved at a speed of 300 mm/min, and when the tensile load when the longitudinal dimension of the test piece becomes 75% of the initial dimension is defined as a contracting force to be obtained.

The sex organ of the pet P in the absorbent article 1 is arranged at a position that overlaps the second rising portion 30Y. The second rising portion 30Y comes into contact with the pet P along the waist or sex organ while forming wrinkles.

Here, since the second rising portion 30Y does not have the elastic member and does not contract in the longitudinal direction, the number of wrinkles formed is small compared with the first rising portion 20Y that contracts in the longitudinal direction. Further, in the second rising portion 30Y not having the elastic member, even when wrinkles occur, the position where the wrinkles are formed is easily changed, and the position where the ridges of the wrinkles come into contact with the sex organ is easily changed.

Therefore, even when the sex organ of the pet P is arranged at the position that overlaps the second rising portion 30Y, the rubbing stimulation received by the sex organ from the second rising portion 30Y is easily dispersed, and this makes it less likely to cause skin inflammation.

Further, in the absorbent article 1, urine leakage is suppressed by the presence of the first rising portion 20Y and the second rising portion 30Y.

Therefore, the absorbent article 1 can suppress urine leakage while suppressing rubbing against the sex organ while the absorbent article 1 is put on.

As shown in FIG. 4, the detailed arrangement of respective components in the absorbent article 1 is as follows. In the absorbent article 1, the central axis in the width direction Y is represented by CL1, and the central axis in the longitudinal direction X is represented by CL2. The central part of the absorbent article 1 in the longitudinal direction X refers to the vicinity of the central axis CL2.

First, in the absorbent article 1, many components are arranged line-symmetrically with respect to the central axis CL1 in the width direction Y. A distance A3 from the central axis CL1 to the first joining portion 20X is equal to a distance B3 from the central axis CL1 to the second joining portion 30X. Further, a distance A4 from the first joining portion 20X to an end 10x on the head side A of the main body portion 10 in the width direction Y is equal to a distance B4 from the second joining portion 30X to an end 10y on the bottom side B of the main body portion 10 in the width direction Y.

It should be noted that, as shown in FIG. 4, when measuring the distance from the first joining portion 20X, an end 20a of the first joining portion 20X is used as a reference. The end 20a is a boundary formed in the width direction of the first leakage suppressing portion 20 between a region that is joined to the main body portion 10 (first joining portion 20X) and a region that is not joined to the main body portion 10 (first rising portion 20Y).

Further, when measuring the distance from the second joining portion 30X, an end 30a of the second joining portion 30X is used as a reference. The end 30a is a boundary formed in the width direction of the second leakage suppressing portion 30 between a region that is joined to the main body portion 10 (second joining portion 30X) and a region that is not joined to the main body portion 10 (second rising portion 30Y).

Further, the absorber 13 is arranged line-symmetrically with respect to the central axis CL1 of the main body portion 10 in the width direction Y. That is, the distances from two widthwise ends of the absorber 13 to the central axis CL1 are respectively equal to each other (A5=B5). Further, the distances from two longitudinal ends of the absorber 13 to the central axis CL2 are also respectively equal to each other (C1=D1).

However, the first rising portion 20Y and the second rising portion 30Y are not line-symmetric with respect to the central axis CL1. Specifically, in the central part of the main body portion 10 in the longitudinal direction X, the sum of a distance A1 from the head side end of the absorber 13 in the width direction Y to the first joining portion 20X and a distance A2 from the first joining portion 20X to an inner end 20*b* of the first rising portion 20Y is longer than the sum of a distance B1 from the bottom side end of the absorber 13 in the width direction Y to the second joining portion 30X and a distance B2 from the second joining portion 30X to an inner end 30*b* of the second rising portion 30Y. That is, the relational expression (A1+A2)>(B1+B2) is established.

In the absorbent article 1, at the central part of the main body portion 10 in the longitudinal direction X, the distance A1 is equal to the distance B1, and the distance A2 is longer than the distance B2 (A2>B2).

Further, in the absorbent article 1, in the central part in the longitudinal direction X of the main body portion 10, the distance A1 is shorter than the distance A2, and the inner end 20*b* of the first rising portion 20Y overlaps the absorber 13 in a plan view (A2>A1). Further, in the absorbent article 1, the distance B1 is longer than the distance B2, and the inner end 30*b* of the second rising portion 30Y does not overlap the absorber 13 in a plan view (B1>B2).

At this time, in the central part of the main body portion 10 in the longitudinal direction X, the distance A1 may be longer than the distance B1 (A1>B1). That is, the absorber 13 may be arranged to deviate toward the bottom side B in the main body portion 10.

Further, in the absorbent article 1, in the width direction Y of the main body portion 10, a distance A6 from the outer end of the third joining portion 20Z to the inner end of the first rising portion 20Y may be shorter than the distance B2 (B2>A6). The third joining portion 20Z may be continuous with the first joining portion 20X. In this case, the distance A6 is 0.

In a case where the absorbent article 1 is manufactured such that the distance A6 is shorter than the distance B2, when the absorbent article 1 is folded small at the time of disposal of the absorbent article 1, urine is less likely to leak out from a gap between the third joining portion 20Z and the first rising portion 20Y.

Figure 5:
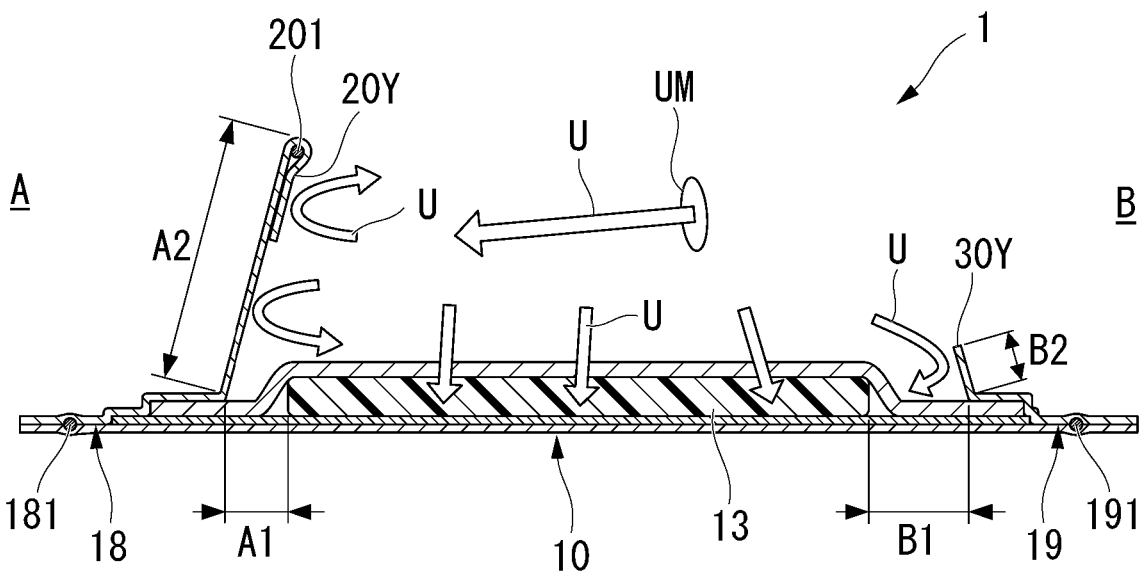
FIG. 5 is an explanatory diagram illustrating another effect of the absorbent article for a pet.
Figure 5:
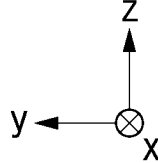

FIG. 5 is an explanatory diagram illustrating another effect of the absorbent article 1, and is a schematic cross-sectional view taken along a central axis CL2 when the absorbent article 1 is put on the pet P. A urethral opening UM of the pet P in the absorbent article 1 is arranged at a position that overlaps the absorber 13, for example. The pet P excretes toward the head side A.

At this time, in the direction in which urination is excreted, a space surrounded by the first rising portion 20Y and the main body portion 10 is formed to block urine U. Since the urine U blocked by the space surrounded by the first rising portion 20Y and the main body portion 10 passes over the absorber 13 in the process of returning to the back side (bottom side B), the urine U is effectively absorbed by the absorber 13. Even when a small amount of urine U not absorbed by the absorber 13 exceeds the absorber 13, the urine U is blocked by the second rising portions 30Y.

Here, as described above, when the relational expression (A1+A2)>(B1+B2) is established, a relatively large space is formed on the head side A with respect to the absorber 13 compared with the bottom side B, and the excreted urine U can be broadly received and blocked. Further, until the urine U is absorbed by the absorber 13, the urine U can be kept in the space surrounded by the first rising portion 20Y and the main body portion 10 even for a short period of time. Therefore, even when the urine U is excreted vigorously, the urine leakage from the head side A can be suppressed. Further, the urine U can be effectively introduced and absorbed into the absorber 13.

(Locking Portion)

Figure 6:
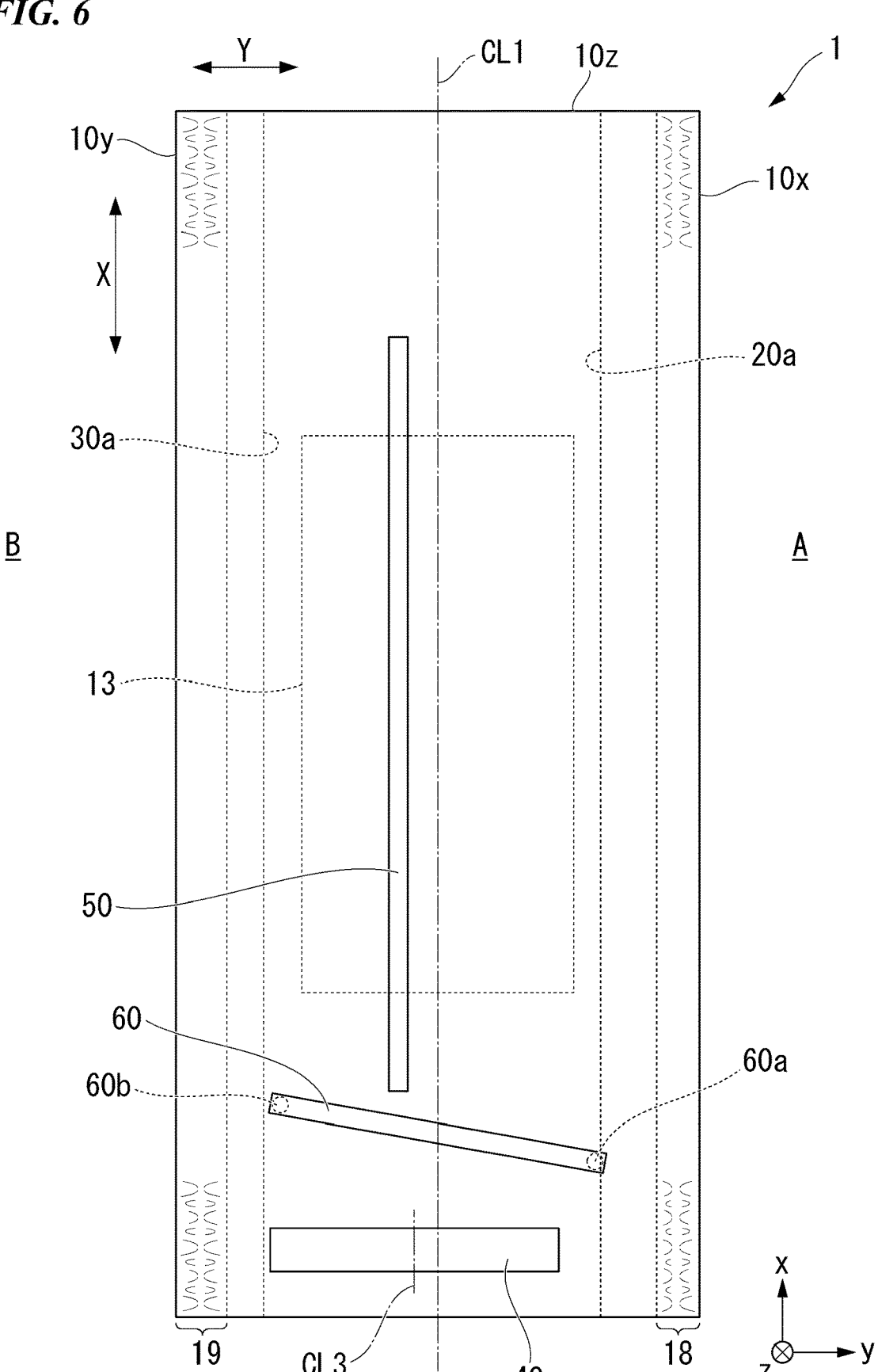
FIG. 6 is a back view of the absorbent article for a pet.

FIG. 6 is a back view of the absorbent article 1. As shown in FIG. 6, the absorbent article 1 has a locking portion 40 on the longitudinal one end side of the main body portion 10. The locking portion 40 is a mechanical fastener. The locking portion 40 connects the top sheet 11 and the back surface layer 12 at two ends of the main body portion 10 in the longitudinal direction X to fix the absorbent article 1 in a cylindrical shape. Therefore, the absorbent article 1 is fixed to the waist of the pet P.

In one or more embodiments, the locking portion 40 is provided in the width direction of the back surface layer 12. Therefore, in the absorbent article 1, when the front surface of the other end side of the main body portion 10 in the longitudinal direction X overlaps the back surface of one end side of the main body portion 10 in the longitudinal direction X, the locking portion 40 is connected to the top sheet 11 and fixed in a cylindrical shape. As described above, when the locking portion 40 is provided on the back surface layer 12, the locking portion 40 is exposed to the outer sides while the absorbent article is put on the pet P. This makes it easier for a user to recognize the locking portion 40 and makes it easier to put the absorbent article on the pet P.

The locking portion 40 may be provided on the top sheet 11. In this case, when the back surface of the other end side of the main body portion 10 in the longitudinal direction X overlaps the front surface of one end side of the main body portion 10 in the longitudinal direction X in the absorbent article 1, the locking portion 40 is connected to the back surface layer 12 and fixed in a cylindrical shape.

In the absorbent article 1, the central axis CL 3 of the locking portion 40 in the width direction Y is positioned on the second joining portion 30X side with respect to the central position (central axis CL1) between the first joining portion 20X and the second joining portion 30X. That is, in the absorbent article 1, the locking portion 40 is provided to deviate relatively toward the bottom side B. Therefore, the absorbent article 1 is fixed on the side closer to the buttocks, and by relatively tightening the side on which the second rising portion 30Y (refer to FIG. 4) is arranged, urine leakage from the back side can be suppressed.

The region in which the locking portion 40 is provided may be uniformly formed, but the configuration in the thickness direction (z-direction) may be different depending on the region. In the absorbent article 1 having the above-described configuration, the stiffness of the region in which the locking portion 40 is provided varies depending on the place, and the absorbent article 1 has a high stiffness region having a relatively high stiffness.

For example, in a case where the locking portion 40 is provided to deviate toward the head side A, a part of the locking portion 40 on the head side A overlaps the first leakage suppressing portion 20 in a plan view, and the rest part does not overlap the first leakage suppressing portion 20. Similarly, in a case where the locking portion 40 is provided to deviate toward the bottom side B, a part of the locking portion 40 on the bottom side B overlaps the second leakage suppressing portion 30 in a plan view, and the rest part does not overlap the second leakage suppressing portion 30 in the plan view. Such a difference in the configuration in the thickness direction causes a difference in stiffness in the region in which the locking portion 40 is provided.

In the above-described example, the stiffness of the region in which the locking portion 40 and the first leakage suppressing portion 20 or the second leakage suppressing portion 30 overlap is relatively high compared with a region in which the locking portion 40 and the first leakage suppressing portion 20 or the second leakage suppressing portion 30 do not overlap. Such a region having a high stiffness corresponds to a "high stiffness region" in one or more embodiments.

In a case where the pet P in the absorbent article 1 moves, a force is applied to the absorbent article 1 from a plurality of directions, and sometimes the absorbent article 1 is pulled and deviate or the end portion thereof is turned up. When the locking portion 40 has the high stiffness region, the high stiffness region is less likely to be deformed than a region having a relatively low stiffness (low stiffness region), and the positional deviation of the absorbent article 1 and the turn-up of the end portion in the vicinity of the high stiffness region can be suppressed.

Further, the high stiffness region may be formed by changing the configuration itself of the locking portion 40. That is, the locking portion may not be uniformly formed but may have portions having relatively different stiffness.

Figure 7:
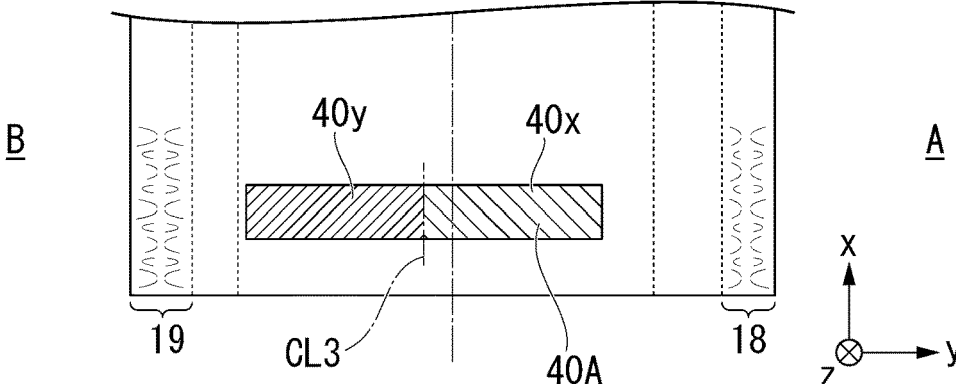
FIG. 7 is an explanatory diagram illustrating a modification of a locking portion.
Figure 8:
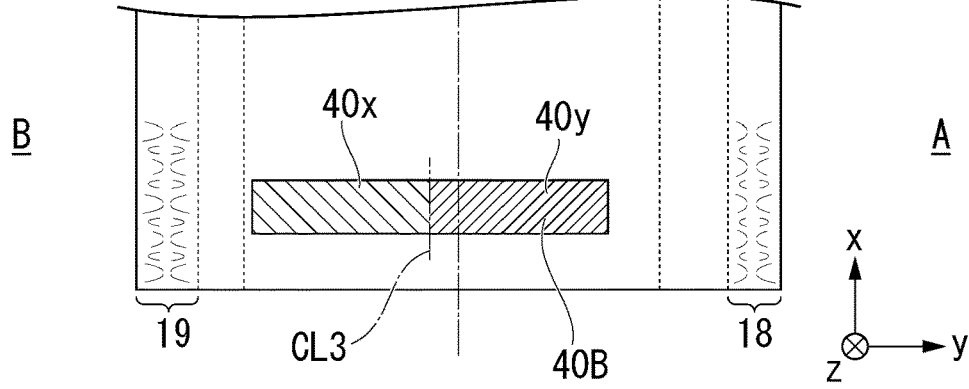
FIG. 8 is an explanatory diagram illustrating a modification of the locking portion.
Figure 9:
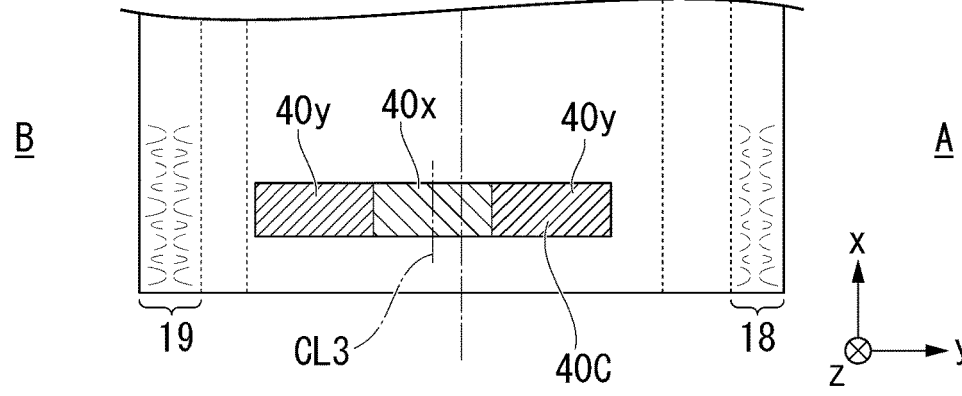
FIG. 9 is an explanatory diagram illustrating a modification of the locking portion.

FIGS. 7 to 9 are explanatory diagrams illustrating modifications of the locking portion. In the following description, a portion having a relatively high stiffness in the locking portion will be referred to as a high stiffness portion. Further, in the following description, in the region in which the locking portion is provided, the configuration of the absorbent article 1 in the thickness direction is assumed to be uniform. That is, the region in which the high stiffness portion of the locking portion is positioned corresponds to the high stiffness region.

In a locking portion 40A shown in FIG. 7, a high stiffness portion 40x is positioned on the head side A in the width direction Y, and a low stiffness portion 40y having a relatively low stiffness is positioned on the bottom side B. While the pet P in the absorbent article 1 is walking, the head side A of the absorbent article 1 is less likely to move compared with the bottom side B. Accordingly, when the high stiffness portion 40x on the head side A is provided, the positional deviation of the absorbent article 1 is suppressed and the absorbent article 1 can be securely fixed to the body.

On the other hand, the pet P moves while swinging the bottom portion laterally while walking. In this case, when the low stiffness portion 40y is provided on the bottom side B, the absorbent article 1 that is put on the pet P can flexibly follow the movement of the body and suppress the positional deviation.

In a locking portion 40B shown in FIG. 8, the high stiffness portion 40x is positioned on the bottom side B in the width direction Y, and the low stiffness portion 40y having a relatively low stiffness is positioned on the head side A. When the absorbent article 1 is put on the pet, first, the back end portion of the absorbent article 1 is positioned by being pressed against the tail of the pet P, and then the first flap portion 18 and the second flap portion 19 are unfolded to fit the absorbent article 1 to the pet. At this time, when the high stiffness portion 40x is present on the bottom side B, the positional deviation can be suppressed when the flap portions are unfolded to fit the absorbent article 1 to the pet.

In a locking portion 40C shown in FIG. 9, the high stiffness portion 40x is positioned in the vicinity of the center in the width direction Y, and the low stiffness portion 40y is positioned on two sides of the head side A and the bottom side B of the high stiffness portion 40x. When the high stiffness portion 40x is positioned in the vicinity of the distal end of the sex organ of the pet P while the absorbent article 1 is put on, the sex organ can be fixed by the high stiffness portion 40x, and accordingly, even when the absorbent article 1 deviates toward the bottom side B, the sex organ is less likely to be exposed.

(Color Change Portion)

As shown in FIG. 6, the absorbent article 1 has a color change portion 50 that reacts with urine and changes the color. The color change portion 50 is provided on the back surface layer 12. The color change portion 50 is a belt-like region that extends in the longitudinal direction X. However, the color change portion 50 is not limited thereto, and various designs can be applied. When confirming the color change of the color change portion 50, the user can recognize a guide for the changing timing of the absorbent article 1.

The color change portion 50 may be positioned on the second joining portion 30X side with respect to the central position (central axis CL1) between the first joining portion 20X and the second joining portion 30X. As described above, when the pet P in the absorbent article 1 excretes urine U, the urine U is first held by the first rising portion 20Y (refer to FIG. 4) on the head side A, and then absorbed by the absorber 13 while returning to the bottom side B. That is, the absorber 13 easily absorbs the urine U on the head side A at first and then easily absorbs the urine U on the bottom side B. Therefore, when the color change portion 50 positioned on the second joining portion 30X side with respect to the central axis CL1 changes the color, it can be determined that the urine U is absorbed by the absorber 13 on the head side A with respect to the color change portion 50, and this makes it easier to appropriately determine that the absorbent article should be changed.

(Mark Portion)

The absorbent article 1 has a mark portion 60. The mark portion 60 is a belt-like printed pattern provided on the back surface layer 12. The mark portion 60 indicates the position of the end of the main body portion 10 in a state where the main body portion 10 is fixed by the locking portion 40. In the absorbent article 1, the top sheet 11 at the other end 10z of the main body portion 10 in the longitudinal direction X overlaps and is fixed to the locking portion 40 in a cylindrical shape, but the mark portion 60 indicates the position of the other end 10z.

When the absorbent article 1 is put on the pet P, the user can use the absorbent article 1 in an appropriate posture by positioning the other end 10z along the mark portion 60.

The mark portion 60 has a first mark portion 60a positioned on the head side A in the width direction Y of the back surface layer 12 and a second mark portion 60b positioned on the bottom side B. In one or more embodiments, the first mark portion 60a and the second mark portion 60b are continuous in a belt-like shape to form the mark portion 60. The first mark portion 60a and the second mark portion 60b may be separated from each other.

The second mark portion 60b is positioned on the inner side of the main body portion 10 in the longitudinal direction X with respect to the first mark portion 60*a*. That is, the belt-like mark portion 60 obliquely crosses the central axis CL1.

In the absorbent article 1, when the other end 10*z* of the main body portion 10 is aligned with the mark portion 60 as described above and is fixed by the locking portion 40, the absorbent article 1 has a spindle shape in which the bottom side B is more tightened than the head side A. Therefore, in a state where the bottom side B on which the second rising portion 30Y is arranged is tightened, the absorbent article 1 is easily put on the pet P, and urine leakage from the bottom side B is easily suppressed.

(Folding Method of Absorbent Article)

FIGS. 10 to 13 are enlarged cross-sectional views showing schematic structures of the vicinity of the second rising portion 30Y. While the absorbent article 1 is stored or sold, the absorbent article 1 is folded in the long side direction and the short side direction in a posture in which the front surface 10*a* is wrapped into the inner side. At this time, the following effect can be obtained by the folding method in the vicinity of the second rising portion 30Y.

Figure 10:
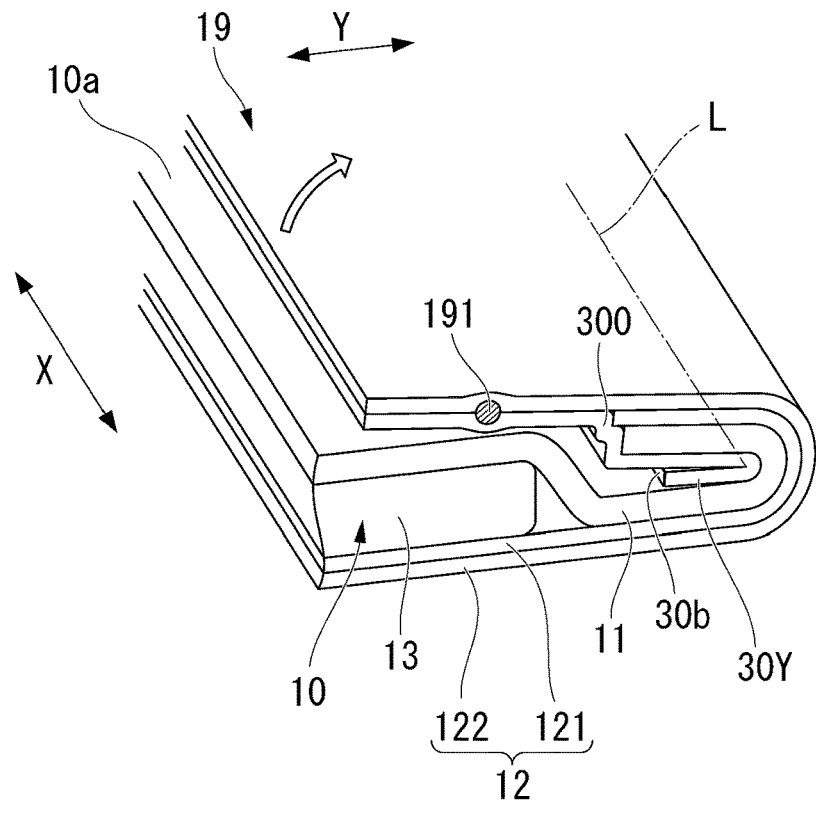
FIG. 10 is an enlarged cross-sectional view showing a schematic structure of the vicinity of a second leakage suppressing portion.
Figure 12:
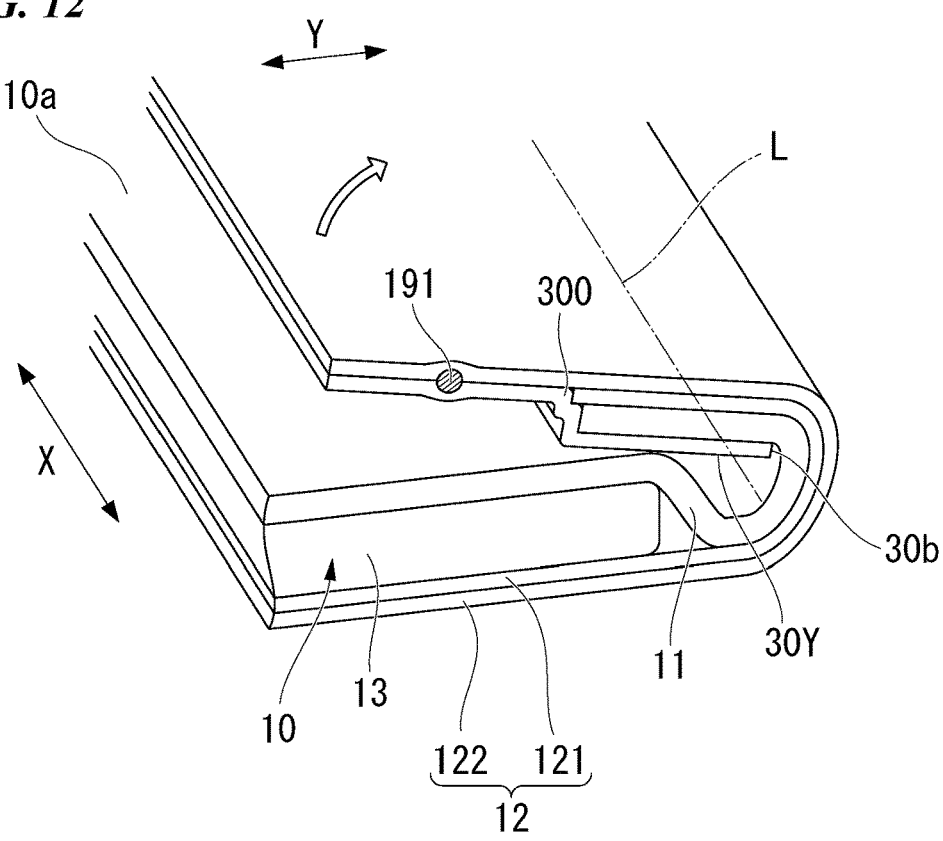
FIG. 12 is an enlarged cross-sectional view showing a schematic structure of the vicinity of the second leakage suppressing portion.

FIGS. 10 and 12 are enlarged cross-sectional views showing a state where the absorbent article 1 is folded. First, in common with FIGS. 10 and 12, the top sheet 11 and the back surface layer 12 are folded back so that the second flap portion 19 faces the front surface 10*a* in a posture in which the top sheet 11 and the back surface layer 12 warp the second rising portion 30Y inside. Due to that, in the absorbent article 1, fold lines L are formed in the longitudinal direction X of the top sheet 11 and the back surface layer 12. The second flap portion 19 corresponds to the "flap portion" in one or more embodiments.

As one method, as shown in FIG. 10, it is considerable that the absorbent article 1 is folded in a posture in which the fold line L overlaps the second rising portion 30Y. In this case, a crease is formed in the second rising portion 30Y due to the fold line L.

Figure 11:
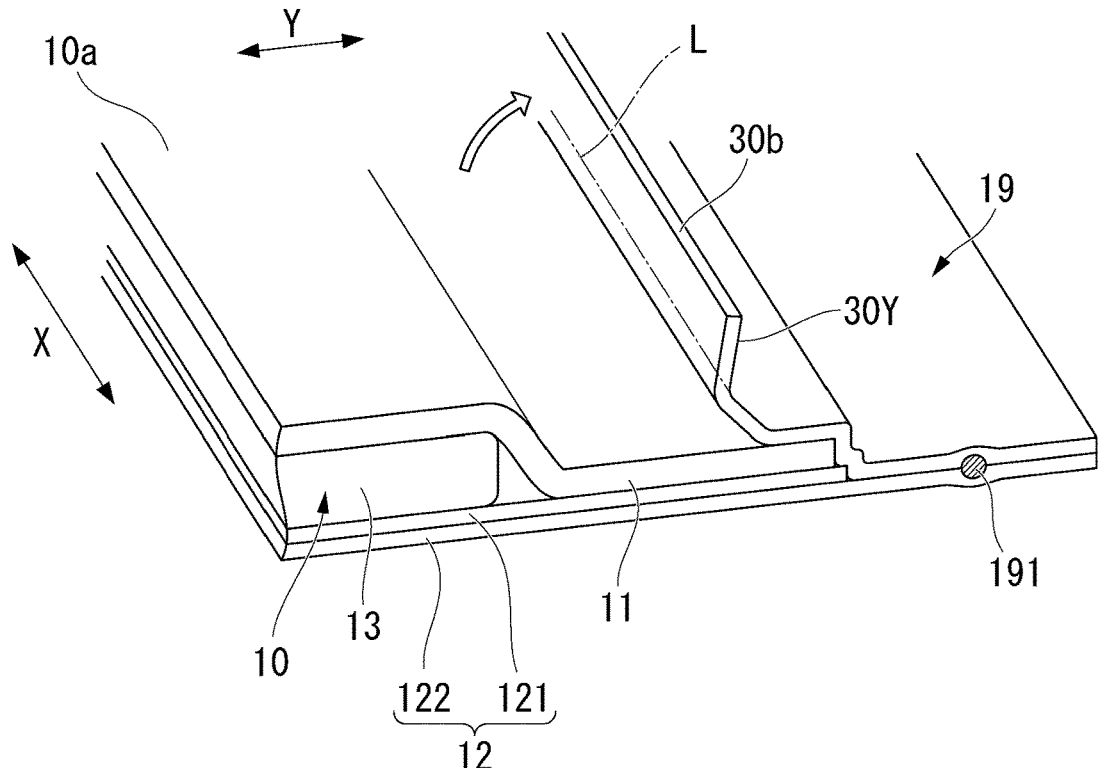
FIG. 11 is an enlarged cross-sectional view showing a schematic structure of the vicinity of the second leakage suppressing portion.

When the absorbent article 1 folded in this manner is unfolded during use, the inner end 30*b* of the second rising portion 30Y is likely to be lifted due to the crease as shown in FIG. 11. Therefore, the absorbent article 1 folded as shown in FIG. 10 can be expected to have the effect that the second rising portion 30Y easily holds urine and urine leakage is easily suppressed.

As another method, as shown in FIG. 12, it is considerable that the absorbent article 1 is folded in a posture in which the fold line L does not overlap the second rising portion 30Y and is positioned on the inner peripheral side of the main body portion 10 with respect to the second rising portion 30Y. In this case, in the second rising portion 30Y, a crease is not formed by the fold line L.

Figure 13:
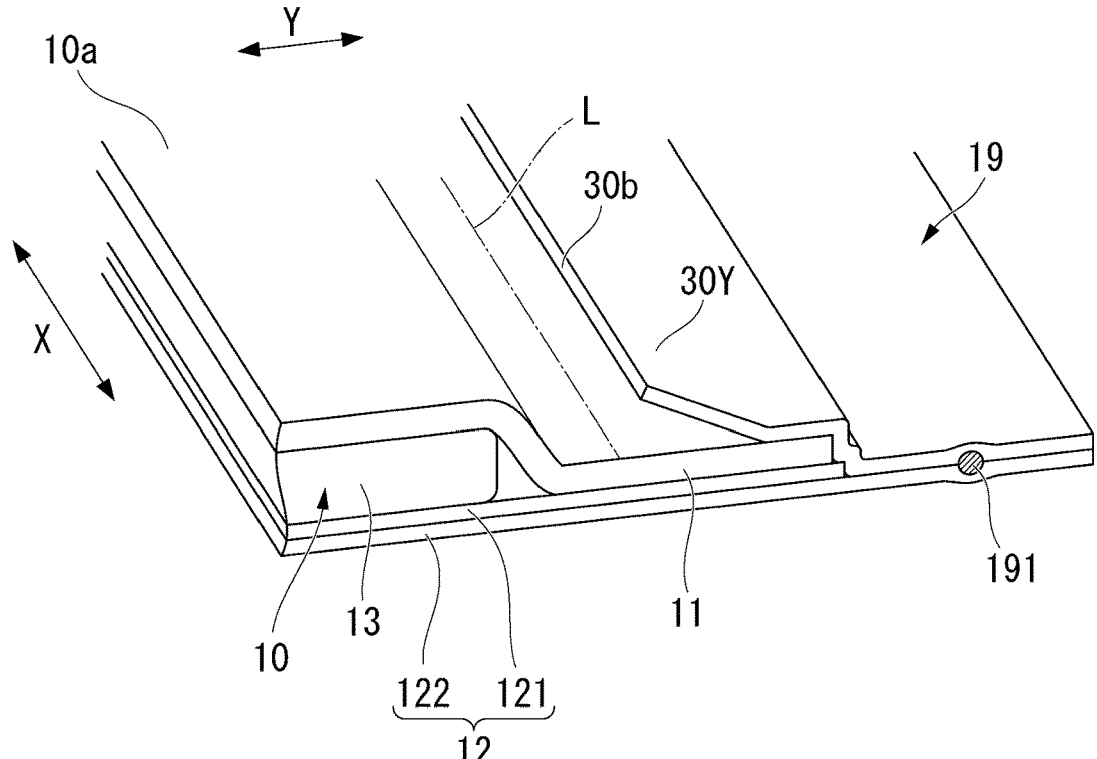
FIG. 13 is an enlarged cross-sectional view showing a schematic structure of the vicinity of the second leakage suppressing portion.

When the absorbent article 1 folded in this manner is unfolded during use, as shown in FIG. 13, the end 30*b* of the second rising portions 30Y is less relatively likely to be lifted compared with the state shown in FIG. 8. Therefore, in the absorbent article 1 folded as shown in FIG. 9, the second rising portion 30Y is less likely to come into contact with the sex organ of the pet P, and even when the second rising portion 30Y comes into contact with the sex organ, the force with which the second rising portion 30Y presses against the sex organ becomes weak. Therefore, the absorbent article 1 folded as shown in FIG. 9 can be expected to have the effect that rubbing against the sex organ is easily suppressed while the absorbent article 1 is put on.

According to the absorbent article 1 having the above-described configuration, rubbing against the sex organ while the absorbent article 1 is put on can be suppressed.

(Modification)

Figure 14:
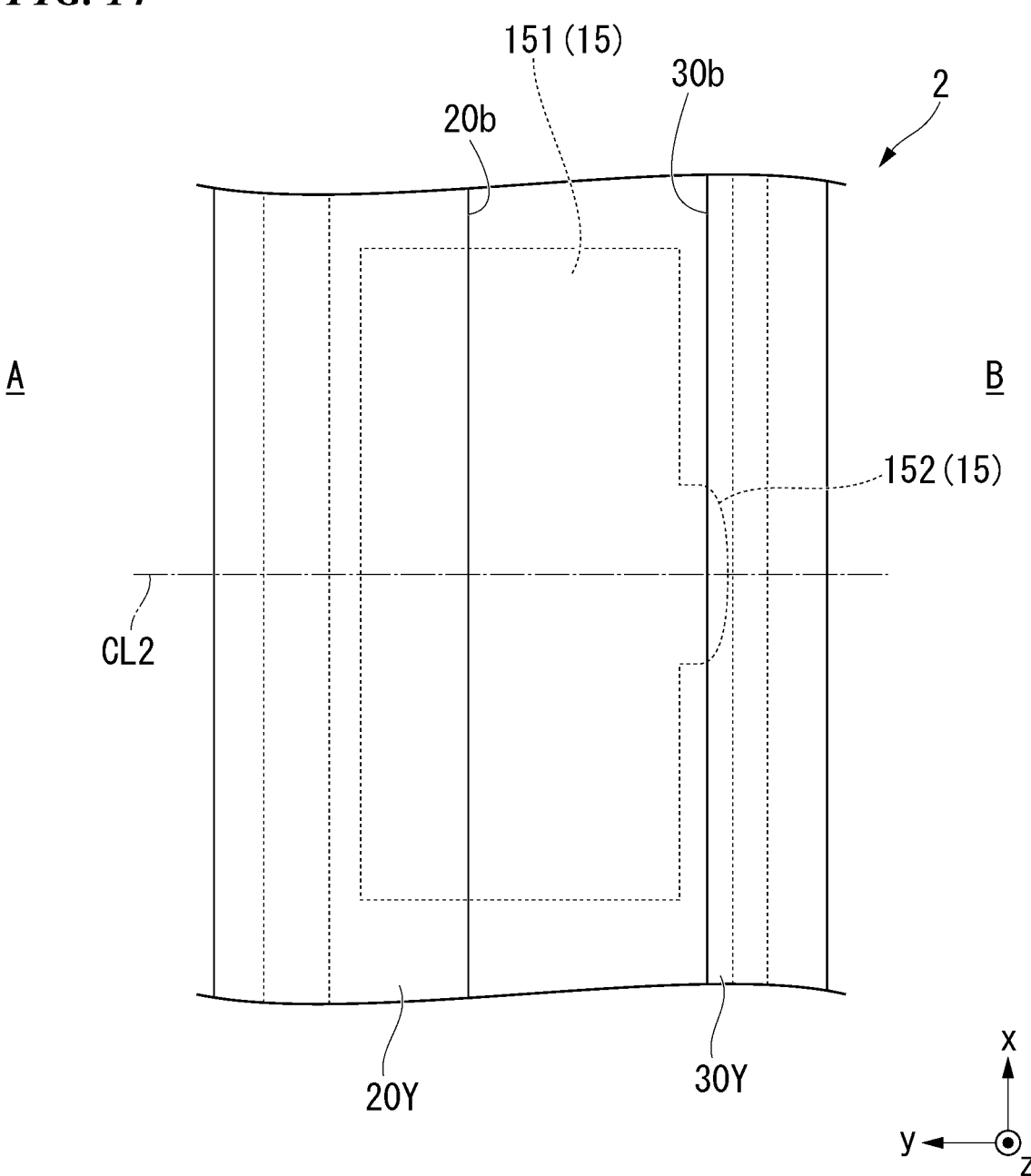
FIG. 14 is a schematic view showing a modification of one or more embodiments.

FIG. 14 is a schematic view showing a modification of one or more embodiments, and is a schematic plan view showing the longitudinal central part of an absorbent article in a plan view.

An absorbent article 2 shown in FIG. 14 has an absorber 15, and the absorber 15 protrudes in the direction of the second leakage suppressing portion 30 at the central part of the main body portion 10 in the longitudinal direction X. That is, the absorber 15 has a first part 151 having a rectangular shape in a plan view, and a second part 152 that protrudes in the direction of the second leakage suppressing portion 30.

In the absorbent article 2, the inner end 30*b* of the second rising portion 30Y overlaps the second part 152 of the absorber 15 in a plan view.

As described above, when the pet P in the absorbent article urinates toward the head side A, the urine U is absorbed by the absorber 13 in the process of being blocked by the first rising portion 20Y and returning to the back side (bottom side B). Here, in a case where the amount of urine U excreted is large or the force of excretion is strong, there is a risk that a large amount of urine U that cannot be absorbed by the absorber 13 exceeds the absorber 13.

Even in such a case, as in the absorbent article 2, when the absorber 15 extends up to the vicinity of the second rising portion 30Y, the chance for the absorber 15 to absorb the urine U increases, the urine U is easily absorbed, and urine leakage from the bottom side B is easily suppressed.

Second Example

Figure 15:
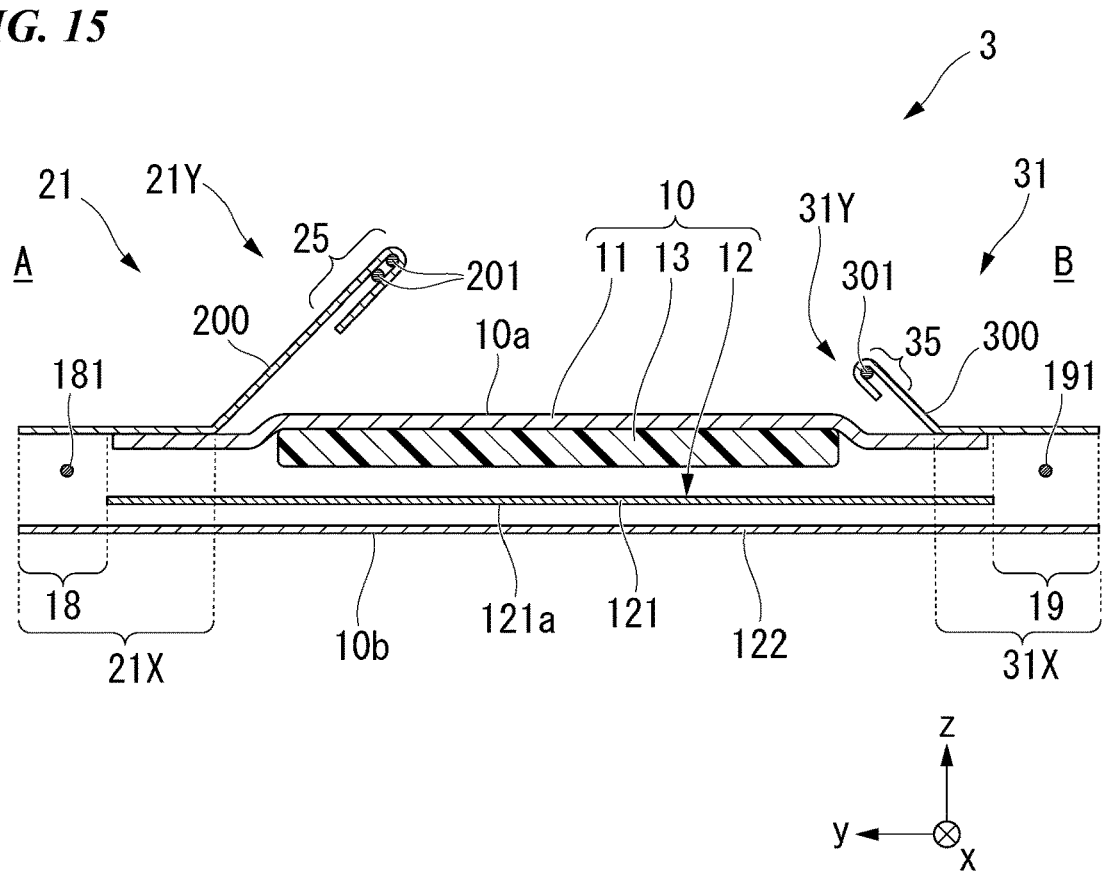
FIG. 15 is an explanatory diagram illustrating an absorbent article for a pet according to one or more embodiments.

FIG. 15 is an explanatory diagram illustrating an absorbent article 3 according to a second example, and is a cross-sectional view in a field of view corresponding to FIG. 3 of the first example. In the present example, constituent elements that are common to those of the first example are denoted by the same reference signs, and a detailed description thereof is omitted.

In the absorbent article 1 of the first example, the first rising portion 20Y contracts in the longitudinal direction, and the second rising portion 30Y does not contract in the longitudinal direction. However, in the absorbent article 3 of one or more embodiments, the first rising portion and the second rising portion contract in the longitudinal direction. That is, in one or more embodiments, the first rising portion may contract in the longitudinal direction of the first rising portion, and the second rising portion may contract in the longitudinal direction of the second rising portion.

As shown in FIG. 15, the absorbent article 3 of one or more embodiments includes a main body portion 10, a first leakage suppressing portion 21, and a second leakage suppressing portion 31.

The first leakage suppressing portion 21 of the absorbent article 3 has a first suppressing portion main body 200 that is formed using a belt-like hydrophobic nonwoven fabric as a material, and a first elastic member 201 that is attached in the longitudinal direction of the first suppressing portion main body 200. The gather portion 25 of the first leakage suppressing portion 21 has two first elastic members 201.

The first leakage suppressing portion 21 has a first joining portion 21X that is a region joined to the main body portion 10 and a first rising portion 21Y that is a region not joined to the main body portion 10.

The first joining portion 21X refers to a region similar to the first joining portion 20X in the absorbent article 1 of the first example. The first rising portion 21Y refers to a region similar to the first rising portion 20Y in the absorbent article 1 of the first example.

The second leakage suppressing portion 31 has a second suppressing portion main body 300 that is formed using a belt-like hydrophobic nonwoven fabric as a material, and a second elastic member 301 that is attached in the longitudinal direction of the second suppressing portion main body. The absorbent article 3 has one second elastic member 301. That is, the number of the second elastic members 301 is smaller than the number of the first elastic members 201.

The second leakage suppressing portion 31 has a second joining portion 31X that is a region joined to the main body portion 10, and a second rising portion 31Y that is a region not joined to the main body portion 10.

The second leakage suppressing portion 31 has a second joining portion 31X that is a region joined to the main body portion 10, and a second rising portion 31Y that is a region not joined to the main body portion 10.

The first joining portion 21X refers to a region similar to the second joining portion 30X in the absorbent article 1 of the first example. The second rising portion 31Y refers to a region similar to the second rising portion 30Y in the absorbent article 1 of the first example.

In the second rising portion 30Y, the end portion on the head side A of the second suppressing portion main body 300 in the width direction Y is folded back along the longitudinal direction X while wrapping the second elastic member 301. For example, the second elastic member 301 is provided in the vicinity of the center of the longitudinal direction X of the second rising portion 31Y, facing the first elastic member 201 of the first rising portion 21Y, and a part of the second elastic member 301 is fixed in a state of being stretched in the longitudinal direction X at the time of manufacturing. The second elastic member 301 is released from the force applied to stretch the second elastic member 301 at the time of manufacturing, and contracts in the longitudinal direction X.

The belt-like region that is the inner end portion of the second suppressing portion main body 300 and is folded-back is joined to the facing second suppressing portion main body 300. In the second rising portion 31Y, a portion to which the second suppressing portion main body 300 is joined while wrapping the second elastic member 301 constitutes a gather portion 35. The gather portion 35 has a configuration known as a three-dimensional gather.

The region in which the gather portion 35 is formed contracts in conjunction with the contraction of the second elastic member 301. Therefore, the second leakage suppressing portion 31 contracts in the longitudinal direction X of the second leakage suppressing portion 31.

As the material of the second elastic member 301, the material similar to the material of the elastic member 201 mentioned above can be used.

In the absorbent article 3 having the above-described configuration, the number of the second elastic members 301 included in the second rising portion 31Y is smaller than the number of the first elastic members 201 included in the first rising portion 21Y. That is, in the absorbent article 3, the longitudinal contracting force of the second rising portion 31Y is smaller than the longitudinal contracting force of the first rising portion 21Y.

The contracting force of the first rising portion 21Y, which is a reference for the relative comparison for the contracting force, can be made equivalent to the contracting force of the three-dimensional gather normally employed in a conventional absorbent article. That is, the contracting force of the second rising portion 31Y is weaker than the contracting force of the three-dimensional gather normally employed in conventional absorbent articles.

In the absorbent article 3 having such a configuration, the second rising portion 31Y has relatively fewer wrinkles than the first rising portion 21Y. Alternatively, in the second rising portion 31Y, even when wrinkles occur, the wrinkles are easily deformed, and the second rising portion 31Y is easily stretched until the wrinkles are no longer present.

Therefore, even when the sex organ of the pet P is arranged at the position that overlaps the second rising portion 31Y, the rubbing stimulation received by the sex organ from the second rising portion 31Y is easily dispersed, and this makes it less likely to cause skin inflammation.

Further, in the absorbent article 3, the contracting forces of the first rising portions 21Y and the second rising portions 31Y are controlled by a difference in the number of elastic members. Therefore, the longitudinal contracting force of the second rising portion 31Y is easily controlled to be smaller than the longitudinal contracting force of the first rising portion 21Y.

Even in the absorbent article 3 having the above-described configuration, rubbing against the sex organ while the absorbent article 3 is put on can be suppressed.

Figure 16:
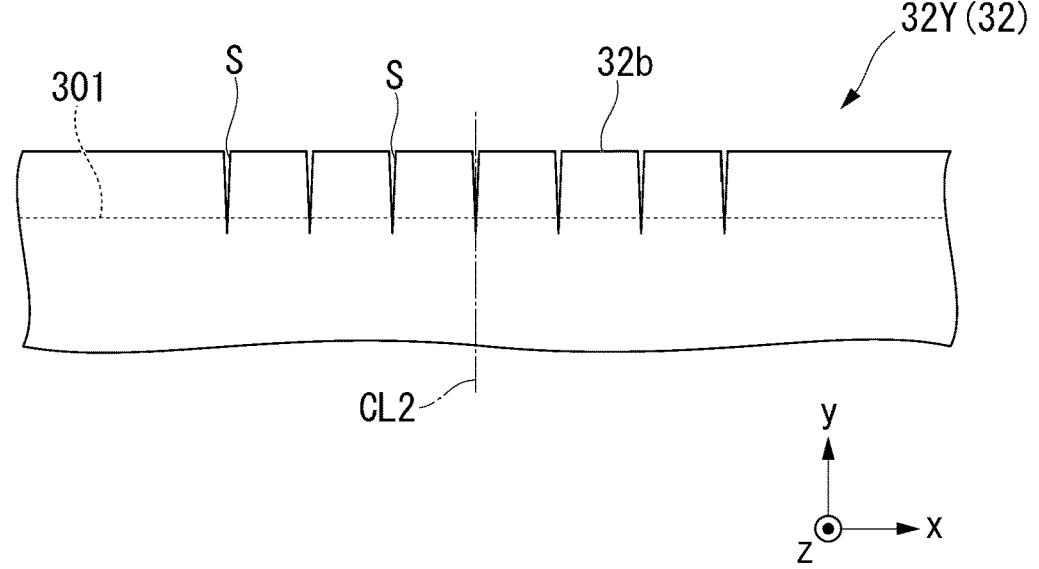
FIG. 16 is a plan view showing a modification of a second leakage suppressing portion.
Figure 17:
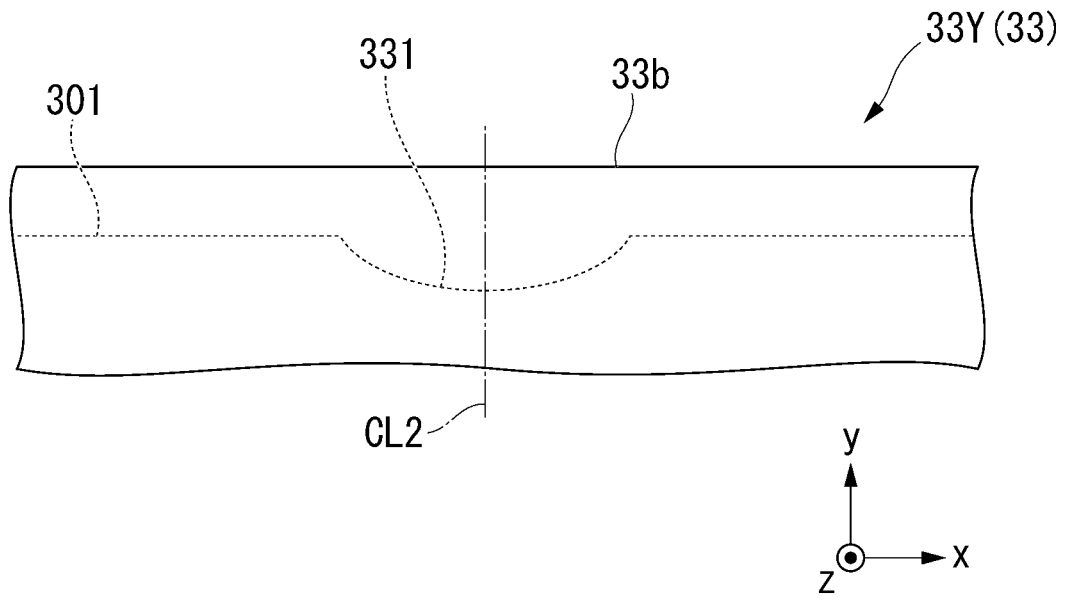
FIG. 17 is a plan view showing a modification of the second leakage suppressing portion.

It should be noted that, as a method for controlling the contracting force of the second rising portion 31Y, the following method can be employed in addition to the number of the elastic members described above. FIGS. 16 and 17 are plan views showing modifications of the second rising portion of the second leakage suppressing portion.

First, as in the second leakage suppressing portion 32 shown in FIG. 16, a plurality of slits S may be provided at an inner end 32b of the second rising portion 32Y, and the second elastic member 301 may be cut at the portions of the slits S. When the number of the slits S is increased and the number of the cut portions of the second elastic member 301 is increased, the contracting force tends to decrease.

Further, as in the second leakage suppressing portion 33 shown in FIG. 17, at the longitudinal central part of the second rising portion 33Y, the second elastic member 301 included in the second rising portion 33Y may be drawn so as to protrude toward the outer side (bottom side). The portion in which the second elastic member 301 protrudes toward the outer side is indicated by reference sign 331.

The second rising portion 33Y has a long distance from the end 32b of the second rising portion 33Y to the second elastic member 301 compared with the portion in which the second elastic member 301 is provided linearly in the longitudinal direction without being drawn in a protrusion shape. Therefore, in a case where the second rising portion 33Y comes into contact with the sex organ of the pet P, compared with the second rising portion in which the second elastic member 301 is linearly provided in the longitudinal direction, the contact area between the nonwoven fabric and the sex organ becomes relatively large. Therefore, in the second rising portion 33Y, the force applied to the sex organ is easily dispersed, and this makes it less likely to cause pain in the sex organ.

In order to obtain the effect similar to the effect of the second rising portion 33Y, the position of the second elastic member 301 may be changed. Specifically, in the second rising portion, the position of the second elastic member 301 may be moved toward the outer side (bottom side) in the width direction Y.

Further, in order to change the contracting force between the first elastic member 201 and the second elastic member 301, at least one of the materials, the thickness, and the weaving method of the first elastic member 201 and the second elastic member 301 may be changed.

Further, the type of the nonwoven fabric that is the material of the first suppressing portion main body 200 and the second suppressing portion main body 300 may be changed.

Alternatively, as the method for controlling the contracting force between the first rising portion and the second rising portion, the method of stretching the first elastic member 201 and the second elastic member 301 at the time of manufacturing may be changed. Even in a case where the same elastic member is used, when the elastic member is fixed in a state of being stretched at the time of manufacturing, the contracting force tends to increase.

Figure 18:
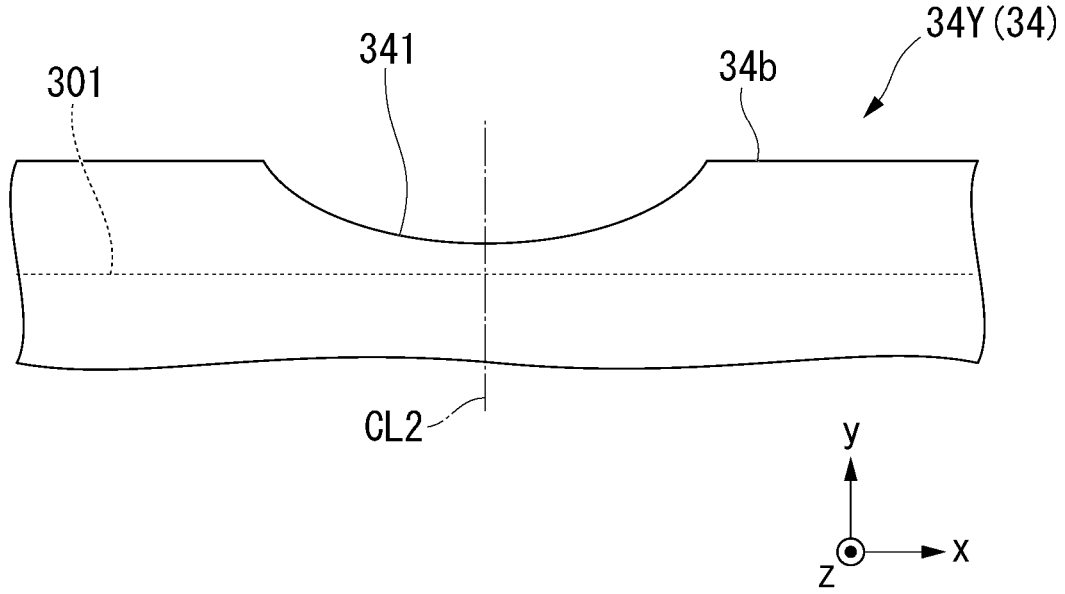
FIG. 18 is a plan view showing a modification of the second leakage suppressing portion.

FIG. 18 is a plan view showing a modification of the second leakage suppressing portion. A second leakage suppressing portion 34 shown in FIG. 18 has a narrow portion 341 having a narrower width at the longitudinal central part of a second rising portion 34Y. The narrow portion 341 is a recessed portion provided at an inner end 34*b* at the longitudinal central part.

In the absorbent article having the second leakage suppressing portion 34, in a case where the absorbent article is put on the pet P, the sex organ of the pet P overlaps the narrow portion 341. Therefore, the second rising portion 34Y is less likely to come into contact with the sex organ of the pet P, and even when the second rising portion 34Y comes into contact with the sex organ, the force with which the second rising portion 34Y presses the sex organ becomes weak. Therefore, the absorbent article having the second leakage suppressing portion 34 can be expected to have the effect that rubbing against the sex organ is easily suppressed while the absorbent article is put on.

Hereinbefore, the embodiments have been described with reference to the accompanying drawings, but the present invention is not limited to the above examples. The shapes, combinations, and the like of the constituent members shown in the above-described examples are merely examples, and various changes can be made based on design requirements and the like without departing from the spirit of the present invention. Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1, 2, 3: absorbent article, 10: main body portion, 10*a*: front surface, 10*b*: back surface, 11: top sheet, 12: back surface layer, 13, 15: absorber, 18: first flap portion, 19: second flap portion, 20, 21: first leakage suppressing portion, 20*a*: end of first joining portion, 20X, 21X: first joining portion, 20Y, 21Y: first rising portion, 20Z: third joining portion, 30, 31, 32, 33, 34: second leakage suppressing portion, 30*a*: end of second joining portion, 30X, 31X: second joining portion, 30Y, 31Y, 32Y, 33Y, 34Y: second rising portion, 40: locking portion, 50: color change portion, 60: mark portion, 60*a*: first mark portion, 60*b*: second mark portion, 121: waterproof film, 122: nonwoven fabric, 200: first suppressing portion main body, 201: elastic member, first elastic member, 300: second suppressing portion main body,

301: second elastic member, 341: narrow portion, P: pet, S: slit, U: urine, X: longitudinal direction, Y: width direction

What is claimed is:

1. An absorbent article for a male pet, comprising:
a liquid-permeable top sheet;
a liquid-impermeable back surface layer;
a liquid absorber disposed between the liquid-permeable top sheet and the liquid-impermeable back surface layer;
a first leakage suppressing portion including:
   a first joining portion that is joined to the liquid-permeable top sheet; and
   a first rising portion that is not joined to the liquid-permeable top sheet, the first rising portion including:
      a first suppressing portion main body having a hydrophobic nonwoven fabric; and
      one or more first elastic members attached in a longitudinal direction of the first suppressing portion main body;
a second leakage suppressing portion including:
   a second joining portion that is joined to the liquid-permeable top sheet; and
   a second rising portion that is not joined to the liquid-permeable top sheet, the second rising portion including:
      a second suppressing portion main body having a hydrophobic nonwoven fabric; and
      one or more second elastic members attached in a longitudinal direction of the second suppressing portion main body; and
a locking portion that connects the liquid-permeable top sheet and the liquid-impermeable back surface layer at two longitudinal end portions such that the absorbent article fully wraps around an entire waist of the male pet, wherein
the absorbent article is configured such that a longitudinal direction of the absorbent article extends along the waist of the male pet wearing the absorbent article,
the first leakage suppressing portion and the second leakage suppressing portion are both disposed on a side of the liquid-permeable top sheet along the longitudinal direction on two widthwise sides of the absorbent article,
a longitudinal contracting force in the second rising portion is smaller than a longitudinal contracting force in the first rising portion,
a first distance from an end of the first joining portion to an inner end of the first rising portion is longer than a second distance from an end of the second joining portion to an inner end of the second rising portion,
the first distance is longer than a third distance from a widthwise head side end of the liquid absorber to the end of the first joining portion,
a fourth distance from a widthwise bottom side end of the liquid absorber to the end of the second joining portion is longer than the second distance, and
a sum of the first distance and the third distance is greater than a sum of the second distance and the fourth distance.

2. The absorbent article according to claim 1, wherein
a total number of the one or more second elastic members is smaller than a total number of the one or more first elastic members.

3. The absorbent article according to claim 2, wherein two short sides of the second suppressing portion main body are joined to the liquid-permeable top sheet, one of two long sides of the second suppressing portion main body is positioned on an outer peripheral side of the liquid-permeable top sheet and is joined to the liquid-permeable top sheet and the liquid-impermeable back surface layer, and the other of the two long sides is positioned on an inner peripheral side of the liquid-permeable top sheet and is not joined to the liquid-permeable top sheet.

4. The absorbent article according to claim 1, wherein the second rising portion has a narrow portion having a narrower width in a central part of a longitudinal direction of the second rising portion.

5. The absorbent article according to claim 1, wherein a flap portion extends in a longitudinal direction of the liquid-permeable top sheet and the liquid-impermeable back surface layer, and is disposed on a widthwise outermost side of the liquid-permeable top sheet and the liquid-impermeable back surface layer, the liquid-permeable top sheet and the liquid-impermeable back surface layer are folded back, the flap portion faces the liquid-permeable top sheet, the liquid-permeable top sheet and the liquid-impermeable back surface layer wrap the second rising portion inside, and a fold line extends in the longitudinal direction of the liquid-permeable top sheet and the liquid-impermeable back surface layer, and overlaps the second rising portion.

6. The absorbent article according to claim 1, wherein a flap portion extends in a longitudinal direction of the liquid-permeable top sheet and the liquid-impermeable back surface layer, and is disposed on a widthwise outermost side of the liquid-permeable top sheet and the liquid-impermeable back surface layer, the liquid-permeable top sheet and the liquid-impermeable back surface layer are folded back, the flap portion faces the liquid-permeable top sheet, the liquid-permeable top sheet and the liquid-impermeable back surface layer wrap the second rising portion inside, and a fold line extends in the longitudinal direction of the liquid-permeable top sheet and the liquid-impermeable back surface layer, and is positioned on an inner peripheral side of the liquid-permeable top sheet with respect to the second rising portion.

7. The absorbent article according to claim 1, wherein the first leakage suppressing portion has, at two longitudinal end portions, third joining portions that join the first leakage suppressing portion with the liquid-permeable top sheet, and a distance from one of the third joining portions to an end of the first rising portion is shorter than a distance from the second joining portion to an end of the second rising portion in a width direction of the absorbent article orthogonal to the longitudinal direction.

8. The absorbent article according to claim 1, wherein the liquid absorber protrudes toward a direction of the second leakage suppressing portion.

9. The absorbent article according to claim 1, wherein the liquid-impermeable back surface layer has a color change portion that reacts with a liquid and changes a color, and the color change portion is disposed on a second joining portion side with respect to a central position between the first joining portion and the second joining portion.

10. The absorbent article according to claim 1, wherein the locking portion is disposed on the liquid-impermeable back surface layer.

11. The absorbent article according to claim 1, wherein the liquid-impermeable back surface layer has a mark portion that indicates a position of a longitudinal end of the liquid-impermeable back surface layer disposed on an outer side in a state of being fixed in a cylindrical shape by the locking portion, the mark portion has a first mark portion positioned on a widthwise head side of the liquid-impermeable back surface layer, and a second mark portion positioned on a widthwise bottom side of the liquid-impermeable back surface layer, and the second mark portion is positioned on a longitudinal inner side with respect to the first mark portion.

12. The absorbent article according to claim 1, wherein a widthwise center of the locking portion is at a second joining portion side with respect to a central position between the first joining portion and the second joining portion.

13. The absorbent article according to claim 1, wherein the locking portion includes a first stiffness region and a second stiffness region having a lower stiffness than the first stiffness region.

14. The absorbent article according to claim 13, wherein the locking portion is disposed in a width direction of the liquid-impermeable back surface layer, and the first stiffness region is positioned on a widthwise head side.

15. An absorbent article for a male pet, comprising:
a liquid-permeable top sheet;
a liquid-impermeable back surface layer;
a liquid absorber disposed between the liquid-permeable top sheet and the liquid-impermeable back surface layer;
a first leakage suppressing portion including:
a first joining portion that is joined to the liquid-permeable top sheet; and
a first rising portion that is not joined to the liquid-permeable top sheet, the first rising portion including:
a first suppressing portion main body having a hydrophobic nonwoven fabric; and
one or more first elastic members attached in a longitudinal direction of the first suppressing portion main body;
a second leakage suppressing portion including:
a second joining portion that is joined to the liquid-permeable top sheet; and
a second rising portion that is not joined to the liquid-permeable top sheet, the second rising portion including:
a second suppressing portion main body having a hydrophobic nonwoven fabric; and
one or more second elastic members attached in a longitudinal direction of the second suppressing portion main body; and
a locking portion that connects the liquid-permeable top sheet and the liquid-impermeable back surface layer at two longitudinal end portions such that the absorbent article fully wraps around an entire waist of the male pet, wherein

23 the absorbent article is configured such that a longitudinal direction of the absorbent article extends along the waist of the male pet wearing the absorbent article, the first leakage suppressing portion and the second leakage suppressing portion are both disposed on a side of the liquid-permeable top sheet along the longitudinal direction on two widthwise sides of the absorbent article, a longitudinal contracting force in the second rising portion is smaller than a longitudinal contracting force in the first rising portion, a first distance from an end of the first joining portion to an inner end of the first rising portion is longer than a second distance from an end of the second joining portion to an inner end of the second rising portion, the first distance is longer than a third distance from a widthwise head side end of the liquid absorber to the end of the first joining portion, the third distance is longer than a fourth distance from a widthwise bottom side end of the liquid absorber to the end of the second joining portion, and a sum of the first distance and the third distance is greater than a sum of the second distance and the fourth distance.

16. The absorbent article according to claim 15, wherein a total number of the one or more second elastic members is smaller than a total number of the one or more first elastic members.

17. The absorbent article according to claim 15, wherein two short sides of the second suppressing portion main body are joined to the liquid-permeable top sheet, one of two long sides of the second suppressing portion main body is positioned on an outer peripheral side of the liquid-permeable top sheet and is joined to the liquid-permeable top sheet and the liquid-impermeable back surface layer, and the other of the two long sides is positioned on an inner peripheral side of the liquid-permeable top sheet and is not joined to the liquid-permeable top sheet.

18. The absorbent article according to claim 15, wherein the second rising portion has a narrow portion having a narrower width in a central part of a longitudinal direction of the second rising portion.

19. The absorbent article according to claim 15, wherein a flap portion extends in a longitudinal direction of the liquid-permeable top sheet and the liquid-impermeable back surface layer, and is disposed on a widthwise outermost side of the liquid-permeable top sheet and the liquid-impermeable back surface layer, the liquid-permeable top sheet and the liquid-impermeable back surface layer are folded back, the flap portion faces the liquid-permeable top sheet, the liquid-permeable top sheet and the liquid-impermeable back surface layer wrap the second rising portion inside, and a fold line extends in the longitudinal direction of the liquid-permeable top sheet and the liquid-impermeable back surface layer, and overlaps the second rising portion.

20. The absorbent article according to claim 15, wherein a flap portion extends in a longitudinal direction of the liquid-permeable top sheet and the liquid-impermeable back surface layer, and is disposed on a widthwise outermost side of the liquid-permeable top sheet and the liquid-impermeable back surface layer, the liquid-permeable top sheet and the liquid-impermeable back surface layer are folded back, the flap portion faces the liquid-permeable top sheet, the liquid-permeable top sheet and the liquid-impermeable back surface layer wrap the second rising portion inside, and a fold line extends in the longitudinal direction of the liquid-permeable top sheet and the liquid-impermeable back surface layer, and is positioned on an inner peripheral side of the liquid-permeable top sheet with respect to the second rising portion.

21. The absorbent article according to claim 15, wherein the first leakage suppressing portion has, at two longitudinal end portions, third joining portions that join the first leakage suppressing portion with the liquid-permeable top sheet, and a distance from one of the third joining portions to an end of the first rising portion is shorter than a distance from the second joining portion to an end of the second rising portion in a width direction of the absorbent article orthogonal to the longitudinal direction.

22. The absorbent article according to claim 15, wherein the liquid absorber protrudes toward a direction of the second leakage suppressing portion.

23. The absorbent article according to claim 15, wherein the liquid-impermeable back surface layer has a color change portion that reacts with a liquid and changes a color, and the color change portion is disposed on a second joining portion side with respect to a central position between the first joining portion and the second joining portion.

24. The absorbent article according to claim 15, wherein the locking portion is disposed on the liquid-impermeable back surface layer.

25. The absorbent article according to claim 15, wherein the liquid-impermeable back surface layer has a mark portion that indicates a position of a longitudinal end of the liquid-impermeable back surface layer disposed on an outer side in a state of being fixed in a cylindrical shape by the locking portion, the mark portion has a first mark portion positioned on a widthwise head side of the liquid-impermeable back surface layer, and a second mark portion positioned on a widthwise bottom side of the liquid-impermeable back surface layer, and the second mark portion is positioned on a longitudinal inner side with respect to the first mark portion.

26. The absorbent article according to claim 15, wherein a widthwise center of the locking portion is at a second joining portion side with respect to a central position between the first joining portion and the second joining portion.

27. The absorbent article according to claim 15, wherein the locking portion includes a first stiffness region and a second stiffness region having a lower stiffness than the first stiffness region.

28. The absorbent article according to claim 27, wherein the locking portion is disposed in a width direction of the liquid-impermeable back surface layer, and the first stiffness region is positioned on a widthwise head side.

* * * * *